[12] United States Patent
Maryanka

(10) Patent No.: US 7,105,008 B2
(45) Date of Patent: Sep. 12, 2006

(54) NASAL CAVITY DILATOR

(75) Inventor: Paz Maryanka, Footscray (AU)

(73) Assignee: ASAP Breatheassist Pty LTD, (AU)

( * ) Notice: Subject to any disclaimer, the term of this patent is extended or adjusted under 35 U.S.C. 154(b) by 114 days.

(21) Appl. No.: 10/631,415

(22) Filed: Jul. 30, 2003

(65) Prior Publication Data
US 2004/0059368 A1 Mar. 25, 2004

Related U.S. Application Data

(63) Continuation-in-part of application No. PCT/AU03/00504, filed on Apr. 30, 2003.

(30) Foreign Application Priority Data
Sep. 19, 2002 (AU) .............................. 2002951517
Jan. 24, 2003 (AU) .............................. 2003900315

(51) Int. Cl.
A61M 29/00 (2006.01)
(52) U.S. Cl. ....................... 606/199; 606/191; 606/198
(58) Field of Classification Search ................. 606/198
See application file for complete search history.

(56) References Cited
U.S. PATENT DOCUMENTS
4,576,168 A 3/1986 Jalowayski
4,759,365 A 7/1988 Askinazy
5,059,193 A * 10/1991 Kuslich ........................ 606/61
5,693,100 A * 12/1997 Pisharodi ................. 623/17.16
5,895,409 A 4/1999 Mehdizadeh
6,129,763 A * 10/2000 Chauvin et al. ......... 623/17.11
6,270,512 B1 8/2001 Rittmann
6,436,142 B1 * 8/2002 Paes et al. ................ 623/17.15
6,821,298 B1 * 11/2004 Jackson ................... 623/17.15
2005/0278028 A1 * 12/2005 Mujwid .................... 623/17.13

FOREIGN PATENT DOCUMENTS
JP 11192251 7/1999

OTHER PUBLICATIONS
Porex Corporation Website, Surgical Nostril Retainers, Dec. 19, 2005, http://www.porexsurgical.com/english/surgical/sprodnoseother.asp.*

* cited by examiner

Primary Examiner—Corrine McDermott
Assistant Examiner—Christopher Prone
(74) Attorney, Agent, or Firm—Morgan, Lewis & Bockius LLP

(57) ABSTRACT

An adjustable nasal dilation device including a first deformable body having one or more ribs able to engage opposing internal sides of a nasal cavity wall when in position and an adjustment member which expands the first deformable body to enlarge the nasal cavity.

3 Claims, 24 Drawing Sheets

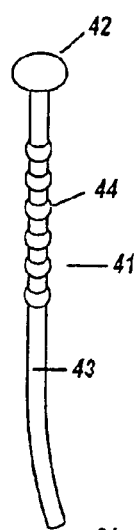
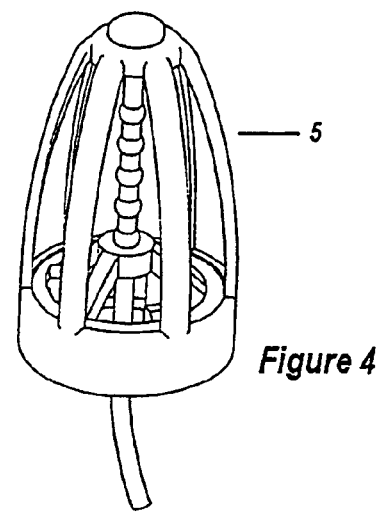
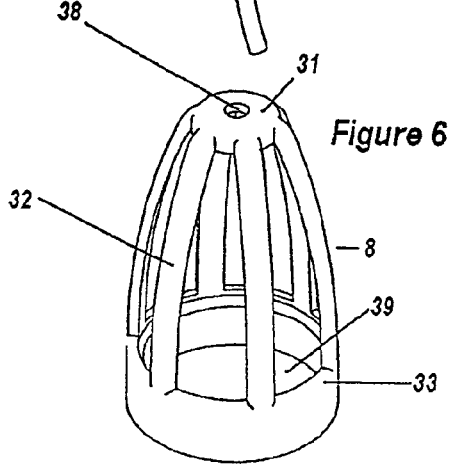
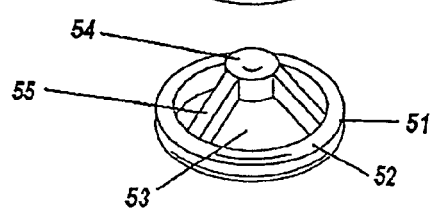
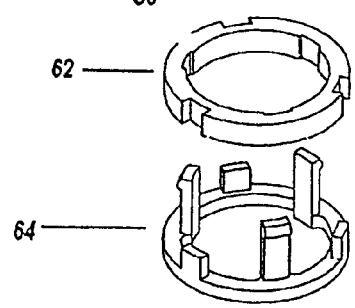
Figure 4
Figure 6
Figure 5

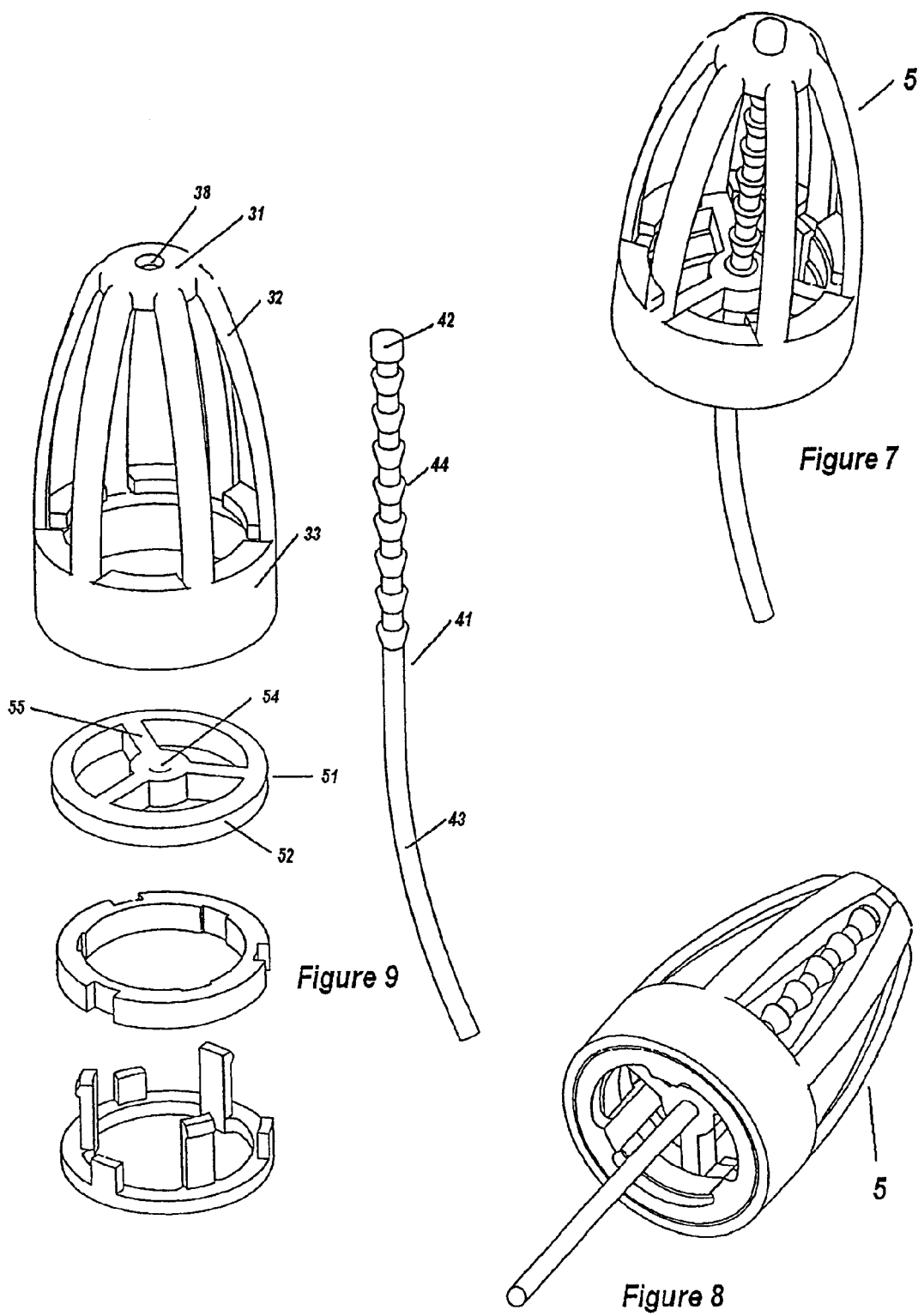

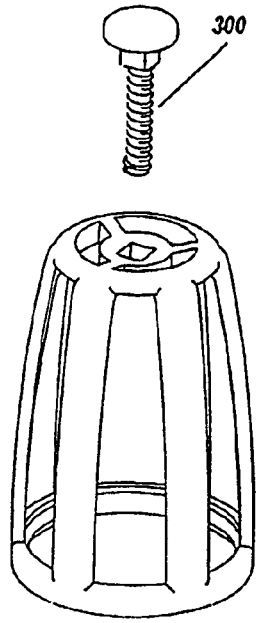
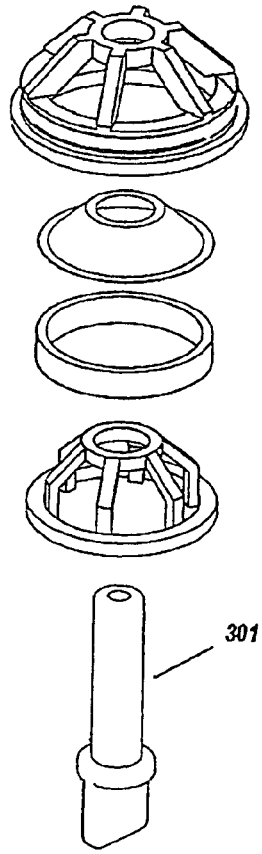
*Figure 12*
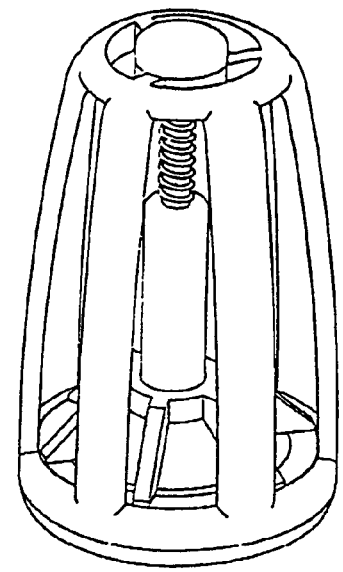
*Figure 10*
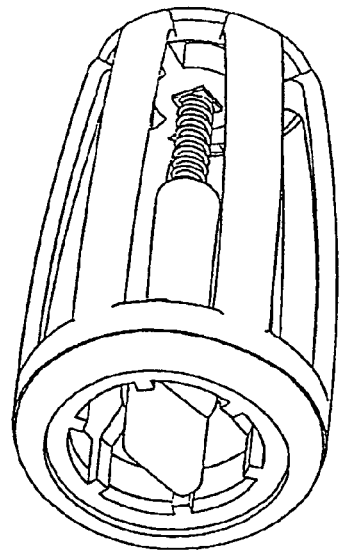
*Figure 11*

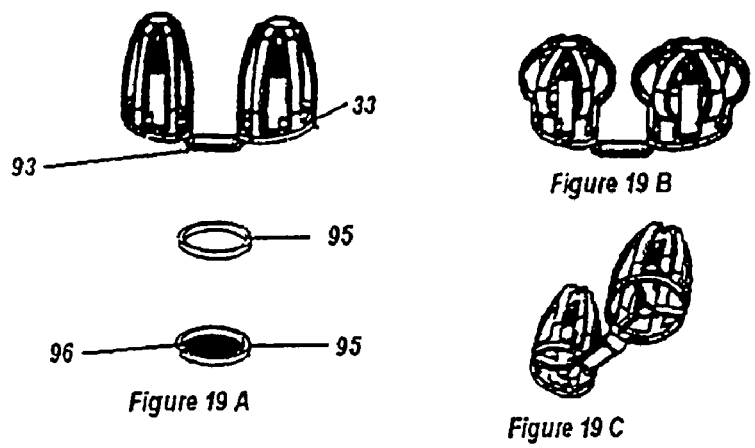
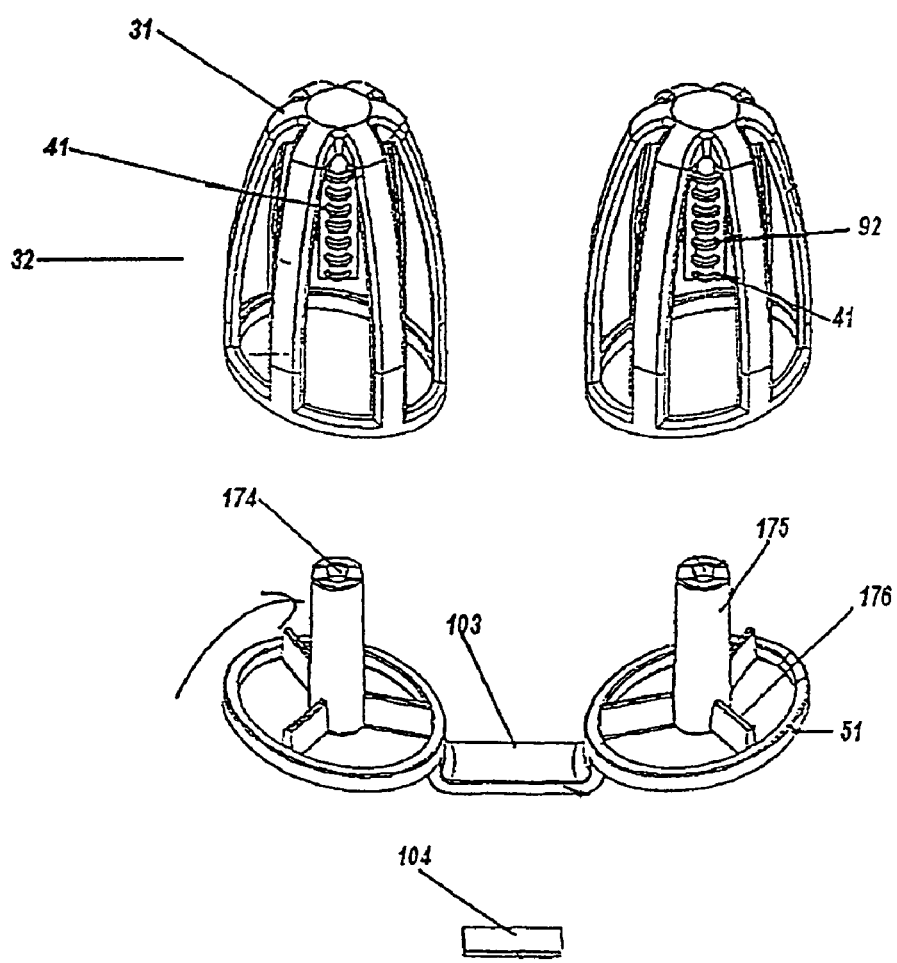
*Figure 20*

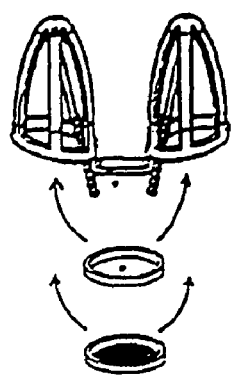
Figure 21 A
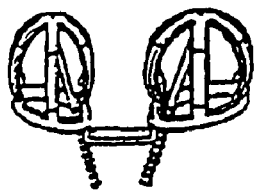
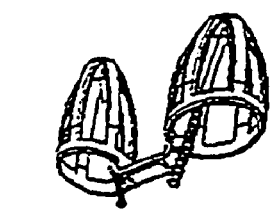
Figure 21 B
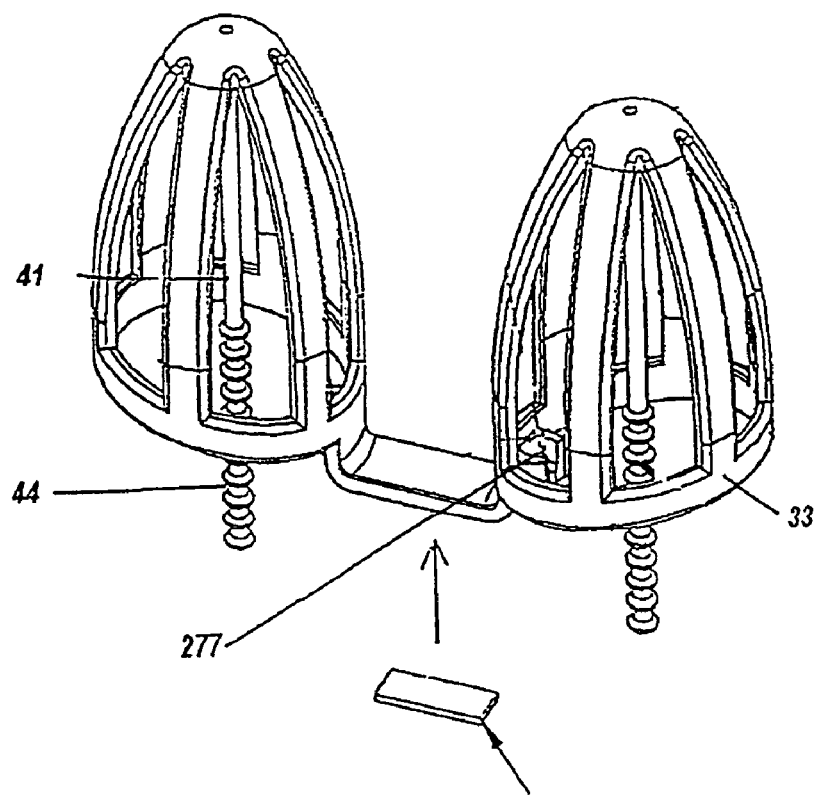
Figure 21 C

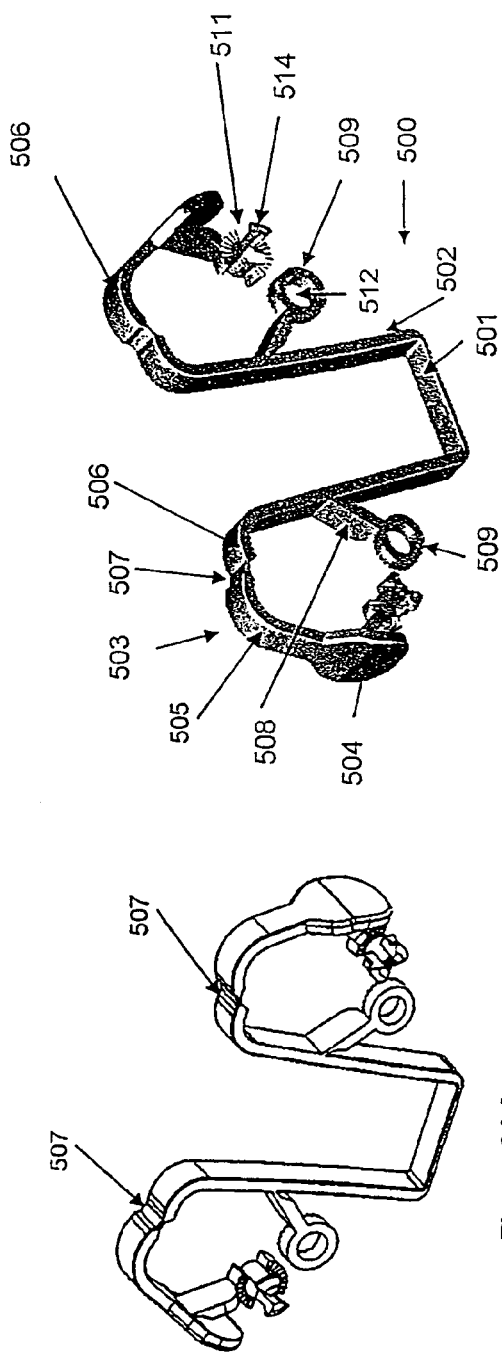
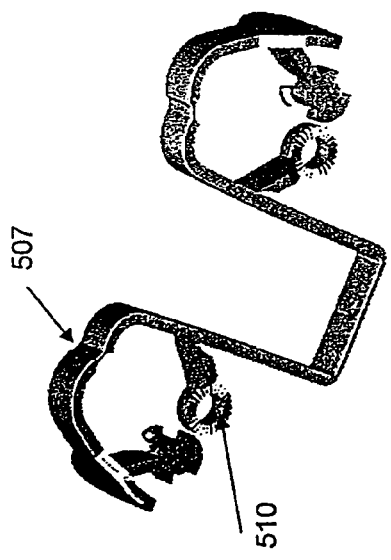
Figure 22 A
Figure 22 B
Figure 24 A

NASAL CAVITY DILATOR

REFERENCE TO RELATED APPLICATIONS

This application is a continuation-in-part of co-pending PCT International Application No. PCT/AU03/00504, filed Apr. 30, 2003, which claimed the benefit of (and accordingly, this application also claims the benefit of) each of Australian Application Nos. 2002951517, filed Sep. 19, 2002 and 2003900315, filed Jan. 24, 2003.

FIELD OF THE INVENTION

The present invention relates to a device, which can be easily adjustable for insertion in a body cavity such as the nasal cavity of a person to dilate the cavity into variable states of dilation and/or to maintain the cavity in a predetermined dilated state.

BACKGROUND OF THE INVENTION

Snoring and general breathing dysfunctions are common ailments that affect a significant proportion of the world's population. People who are disposed to such conditions can be subject to feelings of general tiredness, shortness of breath, fatigue, sleep deprivation, snoring, and even sleep apnoea, which can increase the risks of cardiac arrest.

Attempts have been made to address the above conditions. For instance one option available to sufferers involves a surgical procedure. Apart from requiring a sufferer to endure invasive surgery and the relatively high costs associated therewith, it is documented that surgical procedures are only temporarily successful, sufferers requiring repeated surgery to obtain ongoing relief.

Other methods of addressing snoring, related breathing difficulties arid the like have included nasal sprays. The problem with spray formulations, however, is that they often contain steroidal or vasoconstrictors active agents that cause side effects and can lead to a chronic addiction problem or withdrawal difficulties.

Alternatives to surgical procedures and sprays have included a range of contraptions that can be worn like a mask on the face of a sufferer to help maintain airways in an open condition. These types of devices involve complex designs that are very conspicuous on a wearer. Other types of devices that are worn externally include a resilient plaster applied over the bridge of the nose to externally expand the nostrils. A problem associated with this type of approach is that the plaster is not aesthetically pleasing, and is limited by both the inherent resiliency of the plaster and its ability to exert a sufficient outward force to expand and maintain a nostril cavity in an open condition. In addition the plaster requires painful removal that could result in the tearing of skin.

Other devices are disclosed in patent documents such as a device described in U.S. Pat. No. 5,895,409 that can be inserted within the nasal cavity. This device has a rigid structure and requires manufacturers to make different sized devices to cater for a range of cavity sizes. Also problems frequently arise in a nasal application when a wearer exhibits a deviated septum. A deviated septum is a curvature in the septum, the cartilage and bone that separates the nostrils. A curved septum often renders one nasal cavity a different shape and size to its neighbour and inhibits airflow through one side of the nose and can result in airflow blockage through one nostril. Prior art devices, of the type disclosed in U.S. Pat. No. 5,895,409 that are insertable within the nasal cavity, suffer the drawback that if one dilator of a symmetrical pair, to be inserted, is of a sufficiently small size to enter one nostril then the remaining dilator of the pair is too small to be effective in dilating the other nostril. Conversely, if one device of a symmetrical pair is sufficiently large to effectively dilate one nostril, its pair is often too large to be inserted in the other nostril.

A similar device is disclosed in U.S. Pat. No. 3,710,799, which describes a pair of open cages joined together by a flexible chain of inter-locked links, the cages being slightly larger than the nostrils but insertable therein so that the nose holds the cages in place. This device confers a deal of discomfort for a wearer upon insertion because the device is generally larger than the corresponding orifice in which it is to inserted. Other devices are available that include a resilient plastic strip with widened ends. This type of device is usually bent prior to insertion to conform to a U-shape with the wide ends being inserted into the nostrils. The extent of dilation of the nostril cavity depends on the resiliency of the plastic to return to its normal configuration. These type of dilators are very uncomfortable for a wearer and the force generated by the resilient plastic often causes irritation to the inside lining of the nose not to mention that the article is conspicuous.

It should be understood that any reference to prior art does not constitute an admission of common general knowledge.

Hence it is an object of the present invention to provide a device, which addresses at least one of the difficulties of the prior art.

A preferred object of the invention is to provide a device which is adjustable by a wearer to fit most nasal cavities as well as each nasal cavity independently and to urge dilation of the cavity to enable passage of air/fluid through the cavity.

SUMMARY OF THE INVENTION

In accordance with the invention there is provided a controllably adjustable nasal cavity dilation device for controllably urging the cavity towards a dilated condition, the device including a body having a wall structure which is capable of expansion upon exertion of an applied force to the body; the body being shaped to enable insertion of the device within the cavity in a first condition to rest against internal walls of the nasal cavity wherein when the body is acted upon by an applied force the wall structure extends laterally of the body in a controlled manner within the cavity to exert a positive pressure against the internal walls thereby to dilate the cavity and control the passage of air there through.

The present invention differs from prior art devices in that the instant device can be inserted within a nasal cavity of a user in a non-compressed condition. Hence upon insertion of the device a wearer experiences substantially no discomfiture. Once the device is inserted within a nasal cavity the device can be adjusted in situ, in a controlled manner by the wearer, to tailor a desirable degree of expansion against nasal cavity walls and hence influence the flow of air and pressure applied to the walls to suit the users requirements. Unlike any prior art device the instant device enables expansion of separate nasal cavities independently particularly where a pair of nasal cavities is asymmetrical due to a deviated septum.

In accordance with the invention there is provided a nasal cavity dilation device for urging the cavity towards an open condition, the device having:

a flexible wall structure with variable geometry which is insertable within the cavity so as to rest within the nasal cavity; and an expansion means engaging with the flexible wall structure wherein the geometry of the device is adjustable by application of a force on the expansion means to cause the flexible wall structure to proceed from a first substantially undilated geometry to adopt a second dilated geometry; and a holding means for maintaining the expansion means and the flexible wall structure in a selected second dilated geometry wherein in the second dilating geometry the device is sized and positionable to exert a positive pressure against the internal walls of the cavity thereby opening the cavity to enable passage of air and/or fluid therethrough and to retain the device in its desired position within the nostril.

The device can be adjusted by applying a force to the expansion means to provide a choice of one of a plurality of second dilated geometries such that the user can select an appropriate size relative to the user's nasal cavity and the holding means can maintain the selected size. Hence the device can be adjusted in situ by a wearer to suit the wearers' specific air flow requirements. The nasal cavity dilation device can include two separate wall structures linked together to form a pair, expansion means and holding means to enable independent adjustment of each wall structure in a pair to suit respective nasal cavities since a wearer may want to dilate one of the pair. A link member can join the two structures together for ease of use and as a safety measure to avoid over insertion. The link means also acts as a safety mechanism to prevent accidental inhalation. In a further variation the link means can also act as the expansion means.

The holding means can be a setting means where a material piece is able to hold a selected position by its nature or after being treated such as heat treated in that position. This can include metallic means, which have a degree of flexibility but retain the position after being flexed. Another means is heat settable plastics such that after selection of the correct size the item is set by insertion in hot water or otherwise.

The holding means in another form is lockable to maintain the flexible wall structure in one of a number of second geometries. An advantage of the holding means is that the geometry of the device can be maintained in an adjusted configuration to enable improved airflow that suits a wearers individual requirements. Hence the amount of adjustability of the device can be controlled by the wearer. The holding means in one such lockable form can be irreversible such as known on security ties or be unlockable.

A substantial benefit in the reversible locking of the holding means is its use in changing the dimensions of the structure when the user has a different condition and the nasal cavity size has changed or where a user over-expands the device prior to insertion; the holding means allows for further fine adjustment. Such a condition can occur due to inflamed sinuses or because of colds, influenza and other nose affecting ailments or due to physical damage such as sunburnt noses, broken or damaged noses. Although it also allows use by different users this is an unlikely event for hygiene reasons.

The invention also provides an adjustable nasal cavity dilation device for urging the cavity towards an open condition including:

a body having a flexible wall structure, the wall structure including a plurality of spaced longitudinal ribs extending between a top frame and a bottom frame with the wall structure being expandable over a wide range of geometries and being insertable within the cavity to rest against nasal cavity walls;

an expansion means comprising a connecting link between the top frame and the bottom frame to engage with the flexible wall structure, the link being used to force the top frame towards the bottom frame causing a change in geometry of the elongated ribs, by application of a force on the expansion means, from a first substantially undilated geometry to a second dilated geometry; and a holding means including a locking means for receiving a part of the link to maintain the relative positions of the top frame and the bottom frame and thereby to maintain the flexible wall structure in a second dilated geometry wherein the device is able to be controllably expanded by the expansion means to act against the cavity walls and thus enable passage of air and/or fluid therethrough and to retain the device in its desired position within the nostril.

Another advantage of the device according to the present invention is that in a first undilated geometry, the device can be easily inserted within any sized cavity such as a nostril. The device can be expanded geometrically in situ or prior to insertion in a controlled manner by a wearer by applying an external force to the expansion means. The expansion means subsequently compresses one end of the frame towards the other. In a geometrically dilated condition, the device is able to both engage the internal walls of a nasal cavity and urge the internal walls outwards to improve the nasal passages for receiving improved airflow.

The invention also provides a device for dilating a nasal cavity, the device having:

an open structure to enable fluid/air to pass therethrough, the structure including a first and opposite ends a resilient flexible wall interconnecting the first and opposite ends of the structure, a holding means engaging at least one end of the open structure, the holding means adapted to retain one end of the structure in a position relative to its opposite end on application of a force thereto;

wherein the device is insertable within the cavity in a first insertable configuration to rest initially within internal walls of the nasal cavity and when a force is applied to the holding means one of the ends of the structure is displaced towards the opposite end and the resilient wall progressively flexes outwardly from the initial insertable configuration to adopt a dilated configuration to exert a positive pressure against internal walls of the cavity.

The first and opposite ends of the device can be interconnected by a wall which is made up of a series of resilient ribs. The pressure exerted by the wall of the device on the walls of the cavity can be both controlled and maintained by locking the ends of the device in a desired position.

The device further includes a locking system that enables the ends of the device to be releasably lockable in a desired state of compression. The locking system consists of mating or interlocking components on the expansion means and on one of the ends of the device to releasably lock the expansion means.

The first and opposite ends of the device are substantially circular in cross-section having circular openings therein. One of the circular ends has a smaller circumferential opening than its opposite end. The first and/or second end(s) can be angled to suit the angle between the septum and adjacent wall of a nostril cavity. The advantage of having an angled end enables the device to be better hidden from an observers view.

The series of ribs forming the wall of the device each describe an arcuate pathway from the enlarged end to the smaller end. This accentuates the disposition of the walls/ribs to extend outwardly when the respective ends of the body of the device are subjected to a compressive force exerted by the expansion means.

The expansion means can include a draw-pull element that passes through both circumferential open ends of the device and exerts a compressive force on one end of the body to urge movement of the one end, in the direction of force, towards its opposite end.

The locking means consists of a length of a moulded plastic draw-pull which extends through the openings in the ends, the draw pull being restricted from complete passage therethrough by a protuberance at one end of the draw pull which is larger than the opening in one end of the device to restrict the passage of the draw pull through the opening in one the end.

The locking system can include a locking ring mounted on the enlarged end of the device, the ring having a first large opening to allow passage of the expansion means and a second small opening to enable locking of the expansion means.

The locking means can alternatively include a series of notches or protuberances on the draw pull element, the protuberances being able to pass through the large opening during compression of the body, the draw pull thereafter being prevented from withdrawal by resting one of the series of protuberances below the second smaller opening. In an alternative embodiment the locking means can include a draw-pull having a series of teeth and a receiving cylindrical member with internal mating teeth members for releasably engaging teeth on the draw pull.

The device can house a means for delivery of a medicated vapour. The advantage of the delivery of medicated vapour by the present device is that any substance such as 'Vapor Rub' can be held away from contact with the skin while allowing inhalation of medicated vapour. Hence the substance is able to function purely as a vapour for inhalation while substantially eliminating irritation that can otherwise be caused by direct contact with the skin. In one instance a medicated delivery system can be mounted on the body of the device. The device can further include a filter. The filter can reduce the amount of airborne irritants that can otherwise infiltrate the bronchial system and cause an allergic reaction. While the filter may cause some restriction in the flow of air, any restriction is offset by the expansion of a nostril as a result of the dilation device.

The device of the invention is suited to any size nostril, is economic, reusable and aesthetically pleasing.

Also the invention provides a variable geometry nasal dilation device for maintaining a nasal cavity in an open condition, the device including
- a resiliently expandable housing structure which allows flow of air/fluid therethrough, the housing structure having an opposing first and second end and at least one wall interconnecting the ends;
- the housing structure being sized relative to the cavity to be insertable and removable within the cavity;
- an expansion means operable on the housing structure to urge one of the first or second ends towards its opposite end in an operating condition to alter the geometry of the structure;
- a locking means for releasably locking the compressing means in a position to maintain the housing structure in a desired altered geometry;
- wherein as one end of the structure is urged towards its opposite end under the operation of a compressive force, the wall progressively extends outwardly to exert an opening force on the cavity wall, the device being able to return to the first geometry by removal of the compressing means to a non-operating condition.

In an alternative according to the present invention there is provided a nasal dilation device for improving air flow through a nasal cavity including:
- a first deformable body and a second deformable body interconnected by a bridge, the first and second deformable bodies being substantially symmetrical about a longitudinal axis extending centrally of the bridge;
- each of the first and a second deformable bodies having an uppermost end forming a collar and a lowermost end forming a waistband greater in diameter than the collar, the uppermost end and lowermost ends being interconnected by a series of spaced ribs, each body further including a hollow cylindrical member mounted to the collar extending along a longitudinal axis of each body towards the lowermost end;
- an adjustable member being a closing compression member for each deformable body having a foot on a central leg which is able to extend into the hollow cylindrical member, the leg including a series of spaced apart circumferential protrusions of external diameter equal to or greater than the internal diameter of the hollow cylindrical member allowing the leg to enter the hollow cylinder so that the protrusions engage the hollow cylinder and the foot engages the internal sides of the waistband or the ribs extending from the collar so that the ribs are deflected outwardly of the body to dilate the cavity to a desired size.

The ribs can be extendable in a direction outwardly relative to the body as the leg of the compression member progressively enters the hollow cylindrical member so that the extent of desired dilation of a cavity can be controlled. In this way the degree of expansion of the ribs can be controlled to dilate a cavity to a desired extend.

In a further alternative of the present invention there is provided a nasal cavity dilation device for improving flow of air through a nasal cavity including:
- an elongate U-shape body having an uppermost and lowermost portion, the lowermost portion being sufficiently wide to span a nasal septum, the device including a pair of symmetrical wing members having arcuate sections so that the pair of wings extend downwardly at an angle to the body;
- the body including first and second oppositely disposed and laterally extending resilient arm members and one of the first or second arm members having a recess adjacent its end;
- each wing member having a third arm member extending inwardly towards the first and second arm members so that the third arm member is able to slot between the first and second arm members, the third arm member including a series of ridges separated by adjacent troughs which troughs resiliently and releasably engage the recess on the first or second arm member
- the angle between the body and the wings being controlled and variable by adjusting the engagement between the adjacent troughs and recess to dilate a nasal cavity.

The wing members can include flattened sections which rest against internal nasal cavity walls to improve a wearers level of comfort. The wings can be expanded or contracted either internally or externally of the nasal cavity by urging the teeth against the recess until an adjacent trough engages the recess. The arm containing the recess is sufficiently resilient to enable teeth members to deflect the arm downwards as the teeth act against the recess.

In still a further alternative according to the present invention there is disclosed an adjustable pre-setting nasal cavity dilation device for insertion within a nasal cavity including a body having a flexible wall structure and an expansion means connected to the flexible wall structure wherein when a force is applied to the expansion means the wall structure progressively expands to a desired settable condition laterally of the body to dilate the cavity and substantially improve passage of air there through.

Yet in a further alternative provided by the present invention there is described an adjustable nasal cavity dilation device including a deformable body having a first end and second end connected by a series of spaced resilient ribs, an adjustment member being an expansion means connected to the body which expansion means can be acted upon by an applied force to displace one of the first or second ends towards the other, the ribs being deflected relative to the body to expand the nasal cavity; and a holding means which holds the body in a desired condition, the body being able to return to an unexpanded condition on release of the holding means. This enables substantial improvement of air-flow through a nasal cavity. The expansion means can be connected to the body which expansion means can be acted upon by an external applied force to displace one of the first and second ends towards the other to expand the ribs outwardly relative to the body. Expansion of the device can occur before or after insertion into a nasal cavity.

In yet a further embodiment of the invention there is disclosed an adjustable nasal dilation device including:

a first deformable body having one or more ribs able to engage opposing internal sides of a nasal cavity wall when in position; and an adjustment member which expands the first deformable body to enlarge the nasal cavity.

The adjustment member can include two arm members interengaging from opposing sides of the first deformable body.

The deformable body can include a spine and a rib or wing member.

The adjustable nasal cavity dilation device can include a second deformable body connected to the first deformable body by a substantially U-shaped bridge to form an uppermost portion and a lowermost portion, the lowermost portion being sufficiently wide to span a nasal septum; the uppermost portion ending in a rib member extending downwardly at an angle to the first and second deformable bodies respectively, the first and second deformable bodies being symmetrical about a longitudinal axis extending centrally of the lowermost portion;

each of the rib members having mounted thereto a first arm member extending inwardly, each arm member including a series of ridges separated by valleys;

the first and second deformable bodies each having mounted thereon a second resilient arm member extending oppositely the first arm member towards the rib members, which second resilient arm members include a recess proximal to each end for engaging with a valley between adjacent spaced ridges on a first arm member so that the angle between the rib members and the first and second deformable body is reversibly adjusted by urging the ridges over the recess.

The first and second deformable bodies further can include a third arm member mounted thereon extending outwardly towards respective rib members, each of the third arm members being disposed above the second opposing arm members, each of the third arm members having a protrusion extending below the level of each arm, which protrusion acts as a guide to assist engagement between the first arm members and the second opposing arm members.

The rib members can include an enlarged surface area, which makes contact with nasal cavity walls. The first and second deformable bodies including symmetrical enlarged portions, which are convergent to make contact with internal surfaces of the nasal cavity.

In a further embodiment of the present invention there is disclosed a nasal dilation device for improving air flow through a nasal cavity including: a first deformable body and an adjustment member;

the first deformable body having an uppermost substantially circular open end forming a collar and a lowermost substantially circular open end forming a waistband; a series of spaced ribs connecting between the uppermost and lowermost ends, the body including a central member mounted on the collar and extending longitudinally within the body towards the lowermost end;

the adjustment member being a closing compression member having a holding base and a central leg mounted thereon, which leg is able to extend into the first deformable body with the holding base engaging the waistband of the first deformable body; the leg of the holding base and the central member of the first deformable body having complementary engagement means allowing engagement which causes the holding base to act against the waistband in response to an external force so that the ribs are deflected outwardly of the body to a desired size for dilating the nasal cavity.

The central member of the first deformable body can be hollow and the leg of the holding base can include a series of spaced apart circumferential protrusions of external diameter equal to or greater than the internal diameter of the hollow central member.

The ribs are generally extendable in a direction outwardly relative to the body as the leg of the compression member progressively enters the hollow member so that the extent of desired dilation of a nasal cavity can be controlled. The holding base can include a central platform on which the leg is mounted and extends upwardly towards the central member. The holding base can further include a locking ring interconnected to the platform by a series of radial arms, the locking ring including an annular shoulder that abuts the waistband when the leg engages within the central member. The holding base can also include a recessed protrusion for receiving a vapor delivery system. The nasal dilation device can include a second deformable body interconnected to the first deformable body by a bridge, the first and second deformable bodies being substantially symmetrical about a longitudinal axis extending centrally of the bridge.

BRIEF DESCRIPTION OF THE DRAWINGS

FIG. 4 is a top perspective view of a fully assembled device in accordance with a second embodiment of the invention.

FIG. 5 is a bottom perspective illustration of the embodiment in FIG. 4.

FIG. 6 is an exploded perspective illustration of the device of FIG. 4.

FIG. 7 is a top perspective view of a fully assembled device in accordance with a third embodiment of the invention.

FIG. 8 is a bottom perspective illustration of the embodiment in FIG. 7.

FIG. 9 is an exploded perspective illustration of the device of FIG. 7.

FIG. 10 is a top perspective view of a fully assembled device in accordance with a fourth embodiment of the invention.

FIG. 11 is a bottom perspective illustration of the embodiment in FIG. 10.

FIG. 12 is an exploded perspective illustration of the device of FIG. 10.

FIGS. 19A, B & C, are varying perspective views of a device in accordance with the invention in undilated form and dilated condition.

FIG. 20A is a device in accordance with the invention showing an alternative holding and expanding mechanism.

FIGS. 21A, B & C illustrate a device according to the invention with a alternative holding mechanism.

DETAILED DESCRIPTION OF THE PREFERRED EMBODIMENT WITH REFERENCE TO THE DRAWINGS

Figure 1:
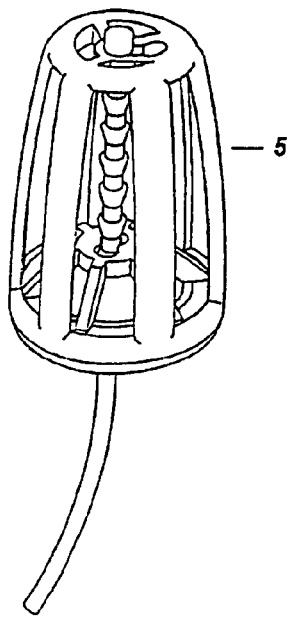
FIG. 1 is a top perspective view of a fully assembled device in accordance with a first embodiment of the invention.
Figure 2:
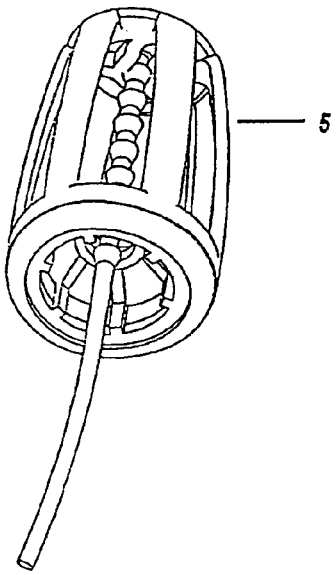
FIG. 2 is a bottom perspective illustration of the embodiment in FIG. 1.
Figure 3:
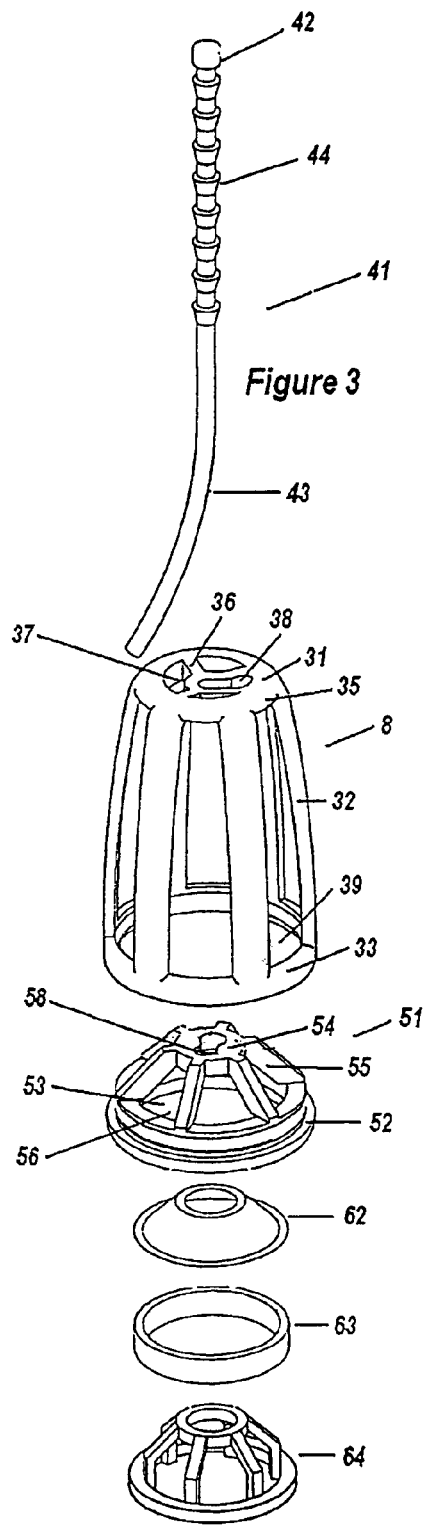
FIG. 3 is an exploded perspective illustration of the device of FIG. 1.

Referring to FIGS. 1, 2 and 3 there is shown a nasal dilation device (5) insertable within a body cavity such as the nose. The nasal cavity dilation device is for urging the cavity towards an open condition. The device has a body (8) with a flexible wall structure formed by a plurality of longitudinally extending elongated ribs (32) extending between a top frame (31) and a bottom frame (33). The top frame (31) has an outer circular collar (35) with inner radial like struts (36) providing flow through openings (37) and a shaped opening forming a mounting opening (38). The bottom frame (33) is a circular waistband with a plurality of elongated spaced ribs (32) connected to the collar (35) and the waist band (33). The ribs at least are made from flexible plastics so that the wall structure has variable geometry. The sizing of the device is such that it is insertable within the nasal cavity.

The nasal dilation device (5) further includes an expansion means comprising a connecting link (41) having a stop (42) larger in dimension than the smooth elongated chord (43) and able to be held in the mounting opening (38). The smooth elongated chord extending in position through the centre of the body (8). At or close to the top of the link (41) between the stop (42) and the smooth elongated chord (43) is a plurality of protuberances (44). In this embodiment the protuberances are spaced sawtooth structure in profile. The plurality of protuberances (44) provide a plurality of locking positions when the smooth elongated chord (43) is pulled forcing the top frame (31) closer to the bottom frame (33) and thereby deflect the elongated ribs such that the geometry of the device is adjusted by application of a force on the expansion means (41) to cause the flexible wall structure to proceed from a first substantially undilated geometry to adopt a second dilated geometry (best seen in FIGS. 17H and 18B).

A holding means in the form of a holding base (51) having a bottom locking ring (52) and radial arm members (55) extending inwardly from the locking ring in a frustoconical configuration to a central platform (54) having a central shaped locking opening (58). The holding base (51) is sized to close off the bottom opening (39) of the body (8) of the device (5) by the locking ring (52) engaging the waistband (33) of the body (8). The shaped locking opening (58) is able to receive a protrusion (44) of the link (41) and thereby maintain the relative positions of the top frame (31) and the bottom frame (33) and thereby maintain the flexible wall structure (32) in a selected second dilated geometry. In the second dilating geometry the device is sized and positionable against and between the internal walls of the cavity and the septum thereby opening the cavity to enable passage of air and/or fluid therethrough.

The device further includes a frustoconical filter (62) with a central opening which is insertable in the central opening (53) of the locking ring (52) of the holding base (51). The filter (62) is held in position by a closing frame (64) similar in structure to the holding base (51) but having a central circular opening rather than a shaped locking opening (58).

It can be seen therefore that due to the frame work structure of the device and in particular the frame work structure of the top frame (31) the holding base (51) and the closing frame (64) and due to the porosity of the filter (62) airflow is available into the nasal cavity. The variable geometry of the wall structure including the ribs (32) is implemented by an expansion means engaging with the flexible wall structure wherein the geometry of the device is adjustable by application of a force on the expansion means to cause the flexible wall structure to proceed from a first substantially undilated geometry to adopt a second dilated geometry.

The filter (62) can be a material such as felt which can in turn be used to deliver medicated vapour such as that derived from "vapour rub"™. Alternatively a filtration device can be inserted within the closing frame to prevent inhalation of dust or pollens which can otherwise initiate allergic reaction by a wearer of the device.

FIGS. 4 to 9 show a nasal cavity device similar to the embodiment of FIGS. 1, 2 and 3 except that instead of having a body 8 that is substantially cylindrical, the body is pyramidal from a circular base to a top point. Another difference is the shape of the protuberances 44 on the link and thereby the change of shape of the shaped locking opening (58). However the operation is substantially identical.

In FIGS. 10 to 12 the link is formed by a screw means (300) extending through and being held by an opening in the top frame and engaging an elongated nut means (301) able to receive the screw and held by an external flange in the bottom frame. By relative twisting of the screw means and the elongated nut the top frame is brought towards the bottom frame and the flexible ribs can be deflected outwards to form a larger dilated second geometry of the required size for the nasal cavity of the user.

Figure 13:
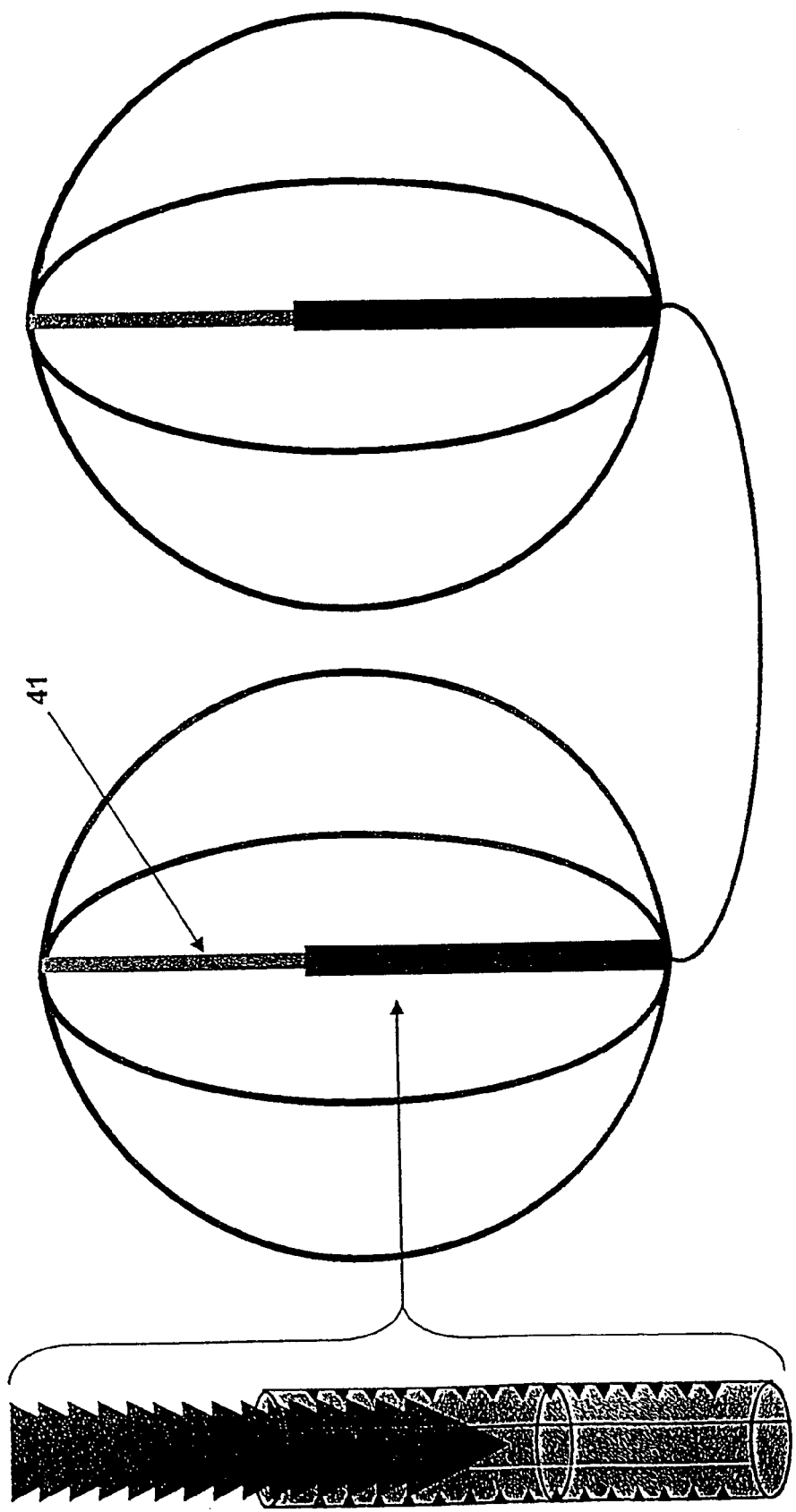
FIG. 13 is a front diagrammatic view of a fully assembled device in accordance with a fifth embodiment of the invention.
Figure 14:
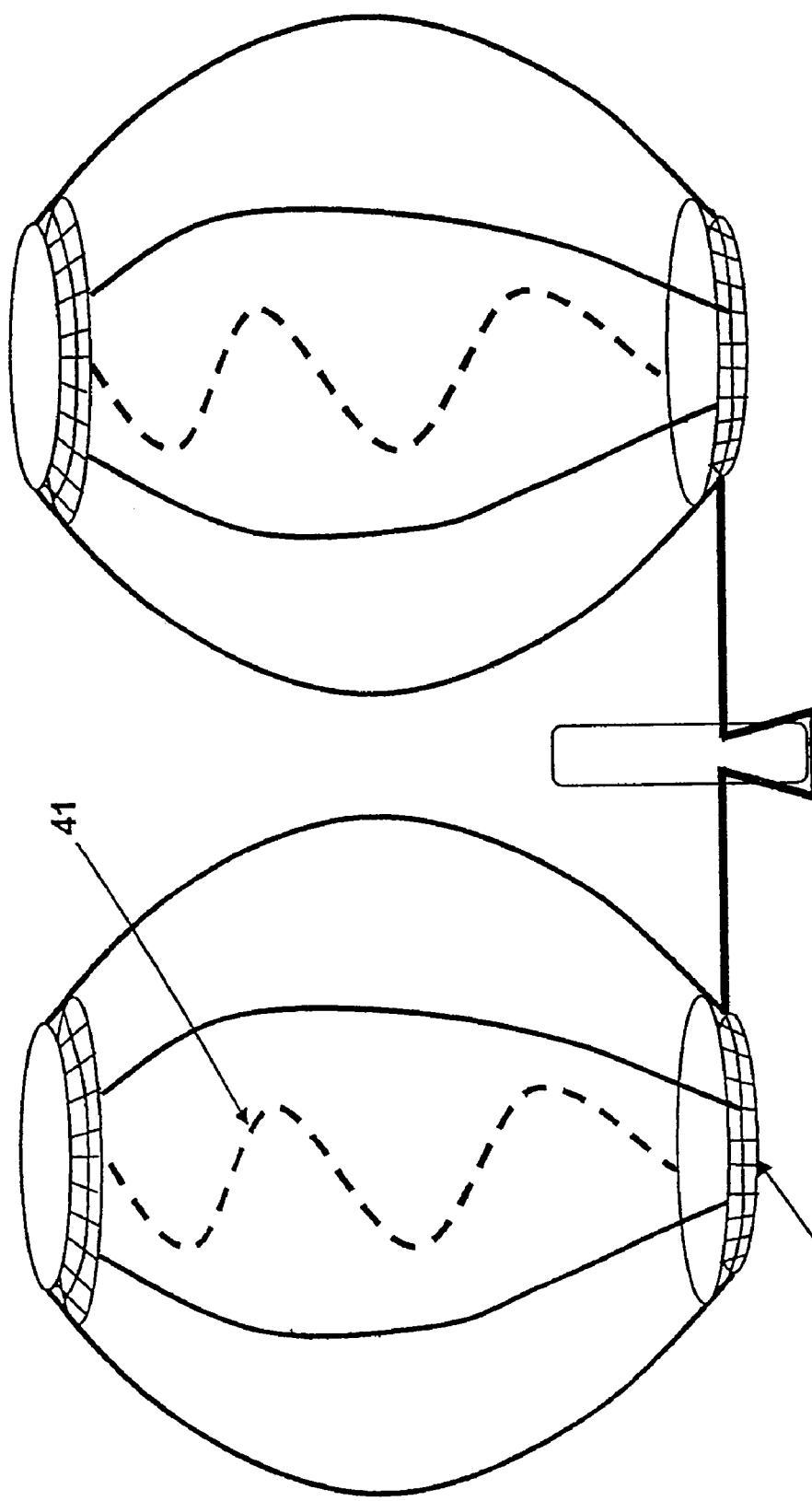
FIG. 14 is a front diagrammatic view of a fully assembled device in accordance with a sixth embodiment of the invention.
Figure 15:
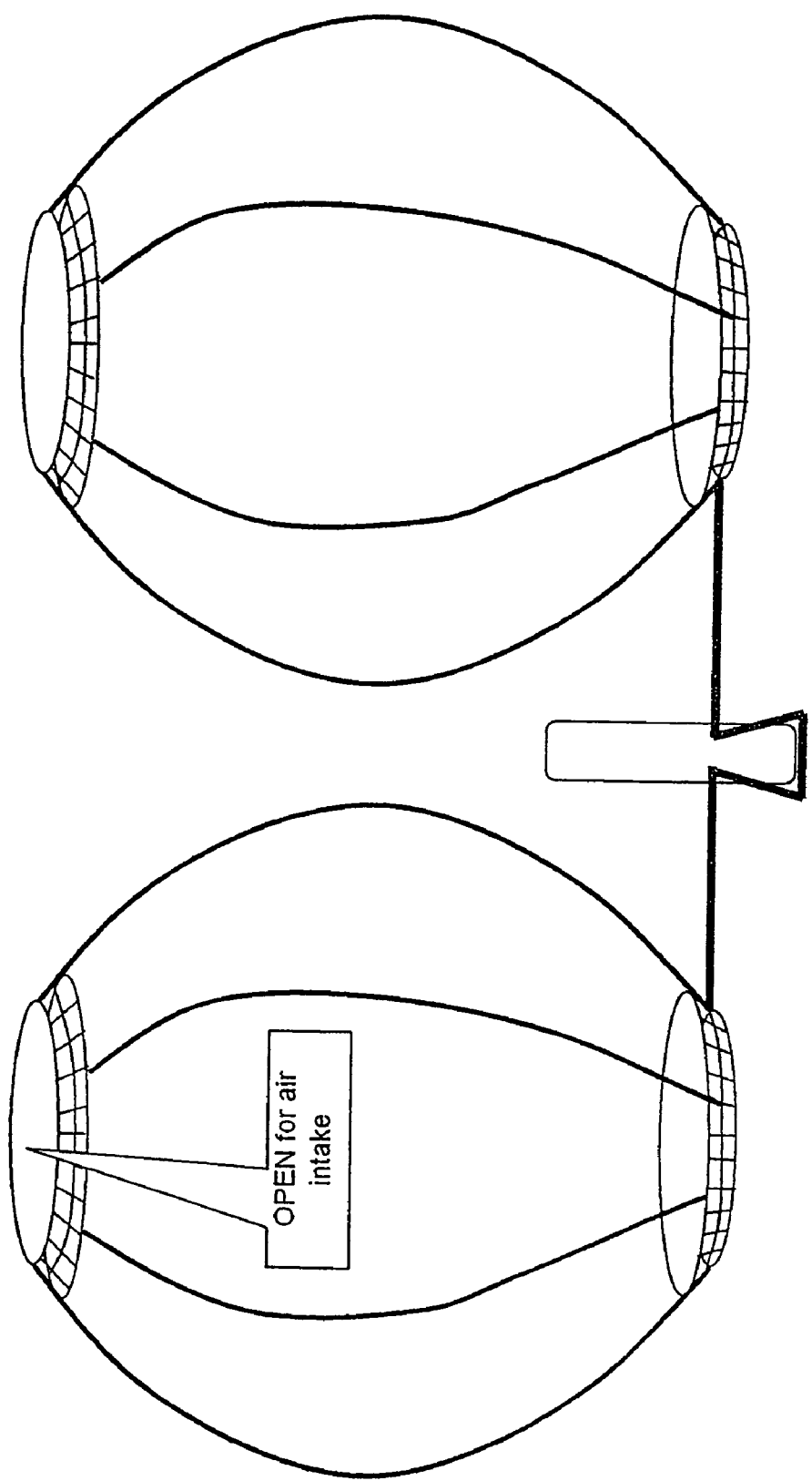
FIG. 15 is a front diagrammatic view of a fully assembled device in accordance with a seventh embodiment of the invention.
Figure 16:
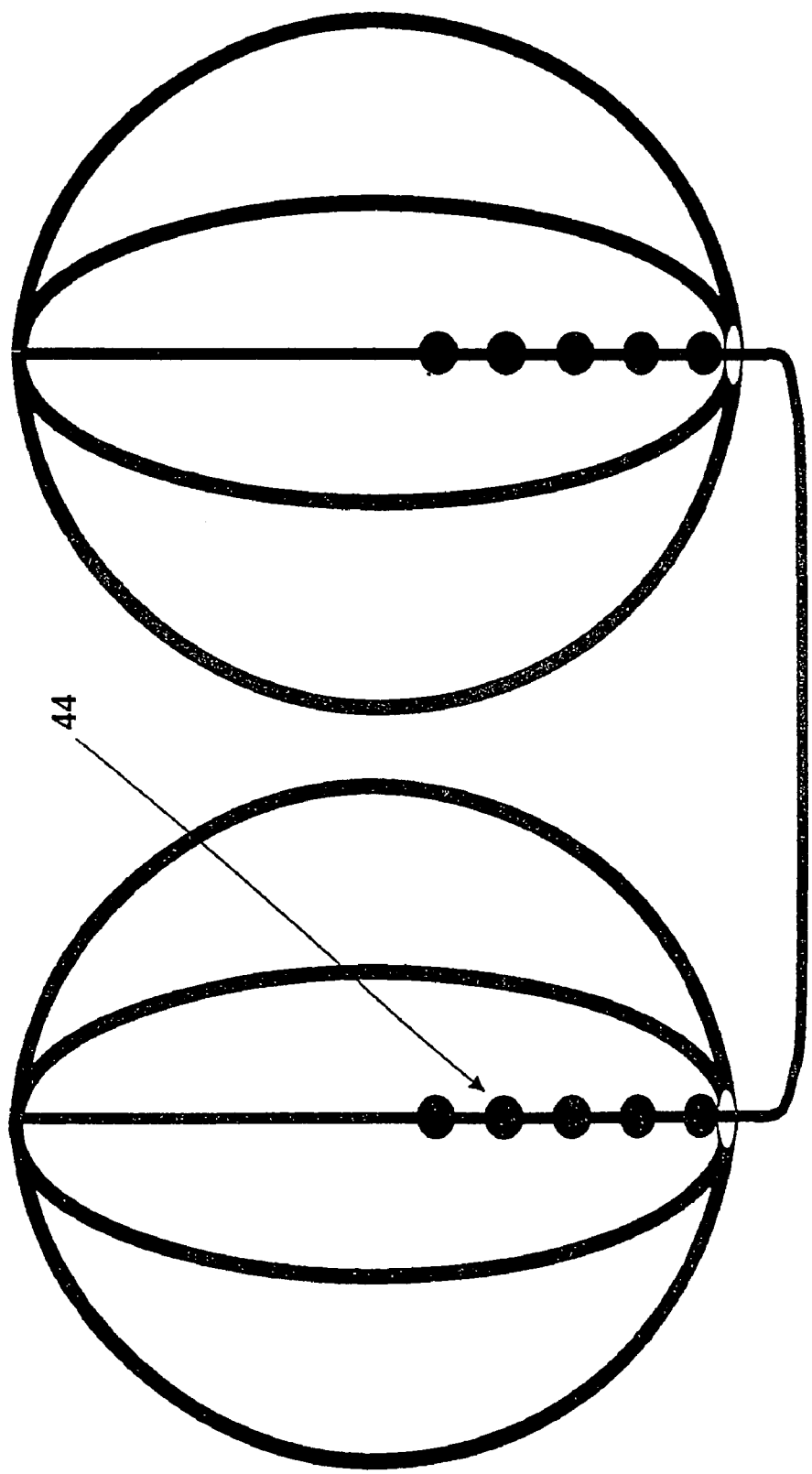
FIG. 16 is a front diagrammatic view of a fully assembled device in accordance with a eighth embodiment of the invention.

In FIGS. 13 to 16 the body structure is substantially spherical with the link (41) being formed of a sawtooth locking means in FIG. 13, a wire means in FIG. 14 that retains its position when the North and South poles of the body of the device are compressed towards each other. In FIG. 16 a plurality of circular protuberances (44) on the link are resistively engageable with an opening at the South pole of the spherical body shape.

Figure 17:
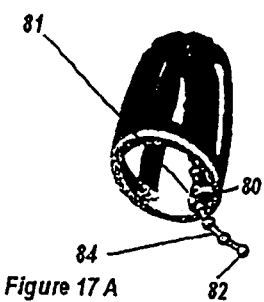
FIGS. 17A, B, C, D, E, F, G&H are varying perspective views of a device in accordance with a ninth embodiment of the invention with FIGS. 17A, B, C, D, E, F, & G being in a first undilated form and FIG. 17H being in a second dilated form.
Figure 17:
Figure 17:
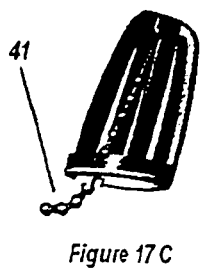
Figure 17:
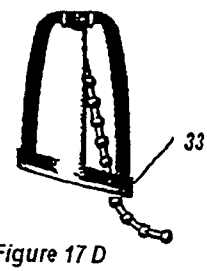
Figure 17:
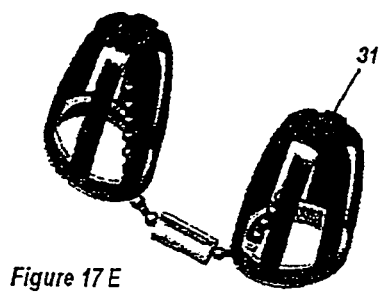
Figure 17:
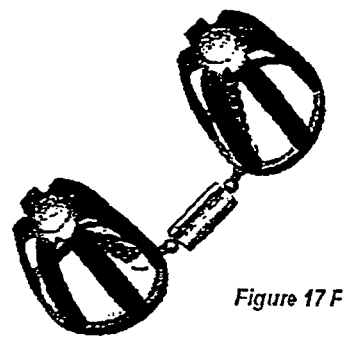
Figure 17:
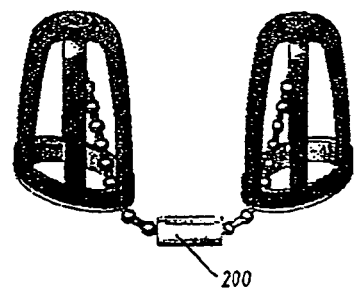
Figure 17:
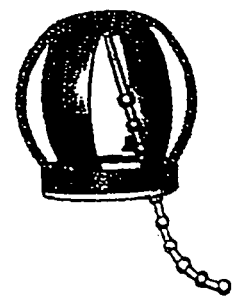

FIGS. 17A, B, C, D, E, F, G&H are varying perspective views of a device in accordance with a further embodiment similar to the initial embodiments. However they are shown in linked pairs for use in each nostril of the user with each link being joined by a joining member (200). In this embodiment pf the invention FIGS. 17A, B, C, D, E, F, & G show the device in a first undilated form and FIG. 17H is in a second dilated form. With particular reference to FIGS. 17C and D there is shown the waistband (33) of the device exhibiting an angled configuration. An advantage of the angled waistband is that some noses exhibit a lower septum relative to the internal wall of an adjacent nostril cavity so that a corresponding angled end frame on the device allows the device to be less obtrusive.

FIG. 17C, in a perspective view, also shows an alternative holding means and expansion means. In this embodiment the expansion means comprises a connecting link (41) that is anchored at one end to the top frame (31) and includes an elongate chord. The chord exhibits a series of spaced apart protuberances (82) along a substantial portion of its length. The holding means comprises a resilient boss or clip (80) integral to and extending from an internal surface of the waistband (33), having an opening (81) to hold the chord. The clip is sufficiently small and resilient to enable a protuberance or even a neck portion (84) of the chord, spaced between adjacent protuberances, to enter to extend in to the opening and thereafter being held captive within the clip to maintain the elongate ribs in a desired condition. Alternatively the opening in the clip is only large enough to accommodate a length of chord between the protuberances, and once a length of chord is placed within the opening, a protuberance, being larger than the opening, rests beneath the opening to prevent the chord from being inadvertently displaced.

In an alternative embodiment (not shown) the waistband can incorporate an opening therein which serves as a holding means. In this embodiment the chord is able to be wedged tightly within the opening in the waistband and thus the chord needn't include any protuberances.

Figure 18:
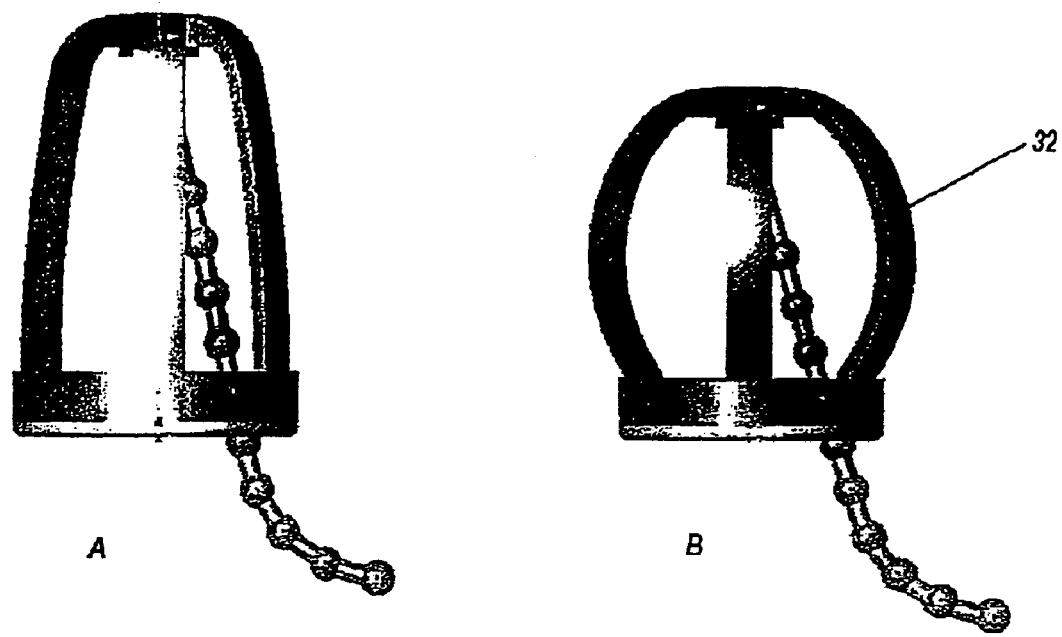
FIGS. 18A & B, are varying perspective views of a device in accordance with a tenth embodiment of the invention with FIG. 18A being in a first undilated form and FIG. 18B being in a second dilated form.

FIGS. 18A & B also show a before use and in use position. FIG. 18A represents a first undilated form showing a substantially cylindrical body shape while FIG. 18B is in a second dilated form in a substantially spherical shape.

Referring to FIG. 18B there is shown a fully assembled device locked in a compressed condition. During the operation of compression, the rib walls (32) move outwardly from the resting geometry of the device to describe an altered geometry akin to a continuous parabolic-shaped curve. In this altered geometry at least a part of the surface area of a rib wall (32) makes contact with the internal surface of the cavity. The rib walls (32) are fabricated from resilient materials such as plastics, which enable them to exert and maintain an opening pressure on the internal surface of the cavity.

Referring to FIGS. 19A, B & C there is shown a device linked in tandem for insertion within nasal cavities one device being joined to the other by a link(93). As is shown the tandem device can include a circumferential ring (95) mountable within the opening defined by the waistband. The ring can include a material such as a felt thereon for retaining a substance capable of delivering a vapour. Alternatively the circumferential ring can include a filter (96) which can be of a desired pore size to reduce inhalation of airborne particulate matter that can otherwise initiate an allergic reaction.

FIG. 20 shows a tandem device having an alternative expansion and holding mechanism. While the principal of operation is similar to that illustrated in FIG. 12 the differences of note are that the elongate link (41) is fixed to the top frame (31) and includes a series of spaced apart protuberances (92) along a substantial part of its length. The link is held in a desired position by a holding means in the form of a holding base (51) with a centrally located upstanding base (175) supported by base cross-members (176). The upstanding base has a centrally located bore (177) with internal mating threads extending along one side of the bore for mating with the protuberances (92) on the link (41). In order to compress the adjustable ribs (32) an external pressure is applied to either the top and/or bottom frame thereby to urge the protuberances within the bore and into mating engagement with the portion of the bore that includes internal threads. To release the device from an expanded condition the bottom frame is rotated so that the protuberances disengage from the internal threads on the one side of the bore and thereafter the protuberances can freely slide to release the link from the bore. The devices are linked together by a nose bridge (103) which includes a recess for housing a vapour dispenser (104).

Referring to FIGS. 21A, B, and C there is shown a modification to FIG. 20 wherein one part of the holding means is a clip (277) positioned on an internal surface of the waistband (33) for receiving a corresponding protuberance (44) on the link (41). FIG. 21B shows the device in a compressed/expanded condition and a non-expanded condition. In both instances the chord is held in a position by locking a protuberance within the clip.

As shown in FIGS. 4, 5 and 6 the device has a resting-geometry in the absence of compression, for enabling easy insertion within a body cavity, although it is understood that the device can be dilated prior to insertion within a nasal cavity. The resting geometry of the structure (4) exhibits a bullet or dome type shape wherein the collar (6) exhibits a smaller relative circumference to the opposite waistband end (7) to facilitate easy insertion of the device within a cavity. In the resting geometry the device (5) is sufficiently small to enable insertion within a very wide range of cavity sizes and thereafter the geometry changes under a force exerted on the top end of the structure by the chord to urge a surface of the ribs against the nasal cavity to improve breathing and air flow within the cavity.

The applicant does not intend to limit the invention to the disclosed embodiments, and any modifications or alterations that are obvious to a person skilled in the art from this disclosure are within the scope of this invention and covered herein.

Figure 22:
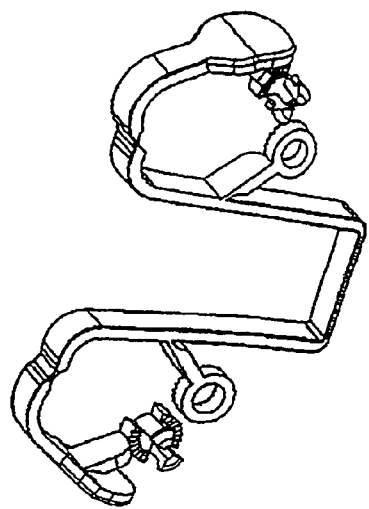
FIGS. 22A B & C are varying perspective views of a device in accordance with a tenth embodiment of the invention illustrating a device in an open condition.
Figure 23:
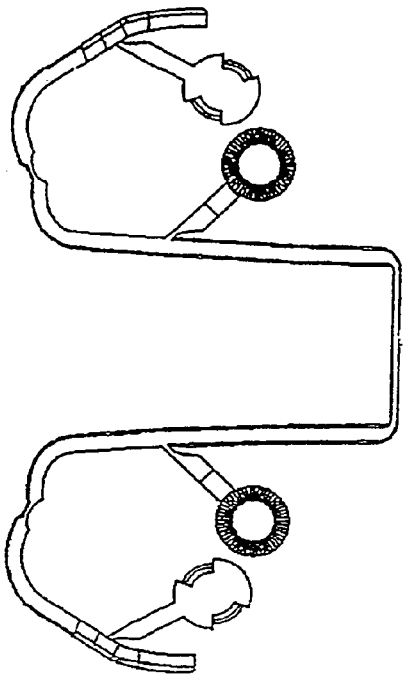
FIG. 23 is an end plan view of the embodiment shown in FIG. 22 in an open condition.
Figure 26:
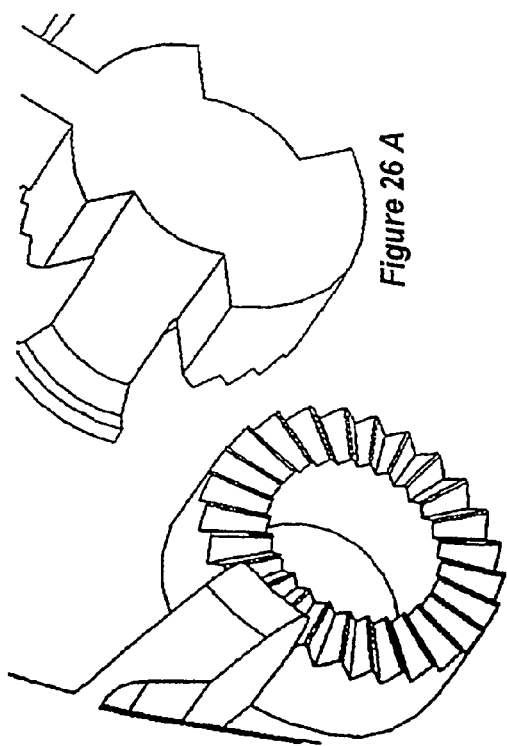
FIGS. 26A & B are magnified perspective views of locking means exemplified in the tenth embodiment.
Figure 26:
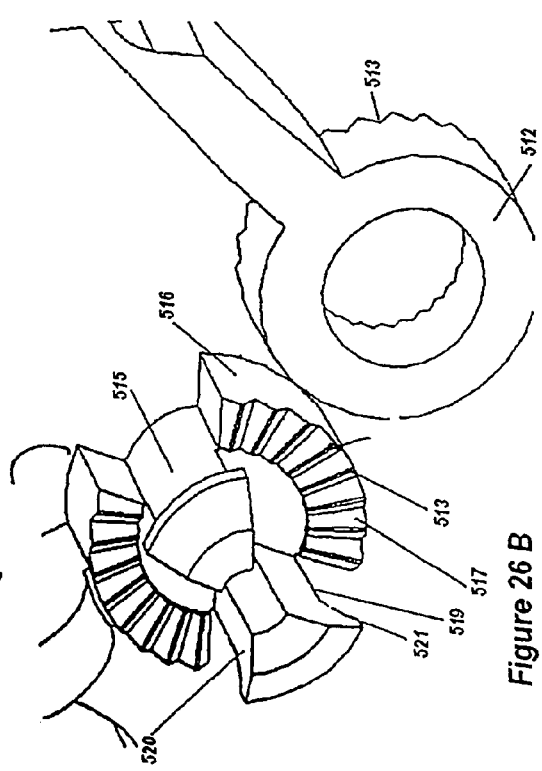
Figure 25:
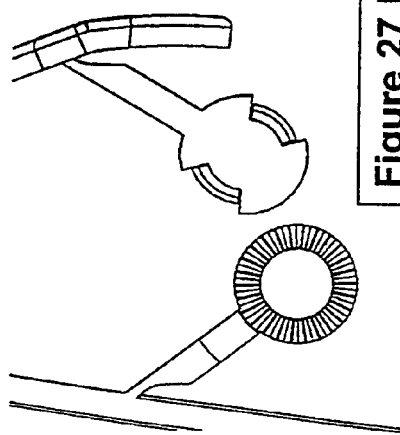
FIGS. 25A & B are end views of the device shown in FIG. 24.
Figure 24:
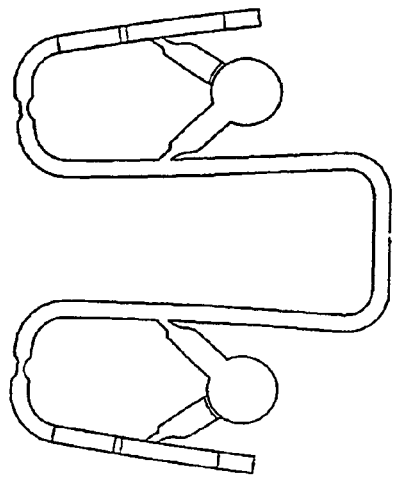
FIG. 24 are varying perspective views of a device, in accordance with a tenth embodiment of the invention, in assembled condition.

Referring to FIGS. 22A, B and C there is shown a device (500) according to a tenth embodiment of the present invention for insertion within a nasal cavity. The device (500) is a unitary device, which can be manufactured in an single step injection moulding process. The device includes a bridge (501) and two upstanding support members (502) extending substantially at right angles to the bridge and exhibiting symmetry about an axis defined by point A-A to form a rigid body structure. The upstanding support members (502) end in shoulders (503). The shoulders (503) generally exhibit an inverted U-shape structure extending from the body distal to the bridge, terminating in an enlarged end (504) which surface area rests flat against internal walls of a nasal cavity without causing discomforture of a user. The shoulders (503) include a first and second curved segments (505) and (506) respectively, separated by a living hinge (507) to enable the second segment (506) of the shoulder to pivot relative to the first segment (505).

The device (500) further includes a radial arm member (508) attached to and extending from the upstanding support members (502) at an acute angle by a living hinge. The arms (508) are able to move in a vertical plane in alignment with the upstanding support member(s), to describe an arcuate pathway. The arms (508) are biased laterally so that the arm, if moved away from the vertical plane defined by the upstanding support member, will be urged back towards its original position.

The arm member(s) (508) end in a circumferential ring (509) having oppositely facing surfaces (513 and 522) surrounding an opening (512). On one surface (513) of the ring (509) there is a series of teeth (510) being interlockable with corresponding mating teeth on a second arm member (511). The second arm member (511) extends from a surface adjacent the enlarged surface area (504) and is angled oppositely to the first arm member (508). The second arm member is joined at a surface near the enlarged surface area (504) by a living hinge which enables the second arm to pivot up and down in a substantially vertical plane. The second arm (511) ends in a protuberance (514) which includes an inner cylindrical core (515) with an outer core (516) encircling at least a part of the external wall of the inner core. The outer core has a first and second opposing face (517, 518) having teeth moulded onto the first face (517) for engagement with corresponding teeth (510) on the arm member (508).

The second arm (511) also includes a flange element (519) extending upwardly from the inner core (515). The flange (519) incorporates a neck (520) which passes through opening (512) in the circular protuberance (509) in an engaged condition, ending in a shoulder (521) that engages a surface (522) of the circumferentical ring (509).

In an operating condition the device (500) requires arm member(s) (508) and (511) to be forced apart laterally against the natural bias so as to allow engagement of mating teeth on respective surfaces of circumferential ring (509) and protuberance (514). Prior to engagement of mating teeth the flange element (519) is passed through the opening (512) until the shoulder (521) of the flange rests against surface (522) of the circumferential ring. Once in an engaged condition the device (500) can be inserted within a users nasal cavity so that the bridge (501) spans the septum of a nose and the upstanding support members (502) bear against internal cavity walls. Once in an inserted condition a force can be applied against the engaged circumferential portions of the arms thereby to cause hinged movement of the arms relative to the support members. As the arms are displaced the interlocking teeth are urged over each other to allow corresponding outward displacement of the shoulder (506) about hinge (507). In this condition the enlarged area (504) of the arm exerts an opening pressure on the nasal wall to expand the nasal cavity.

In this embodiment the device can be retained in the nasal cavity in a suitably expanded state without inadvertent removal. The arms can be maintained in a relative position by the mating locking teeth. The shoulder portion (506) can be hingedly displaced outwardly by exerting a force against the interlocked ring (502) and protuberance (514) so as to enable the enlarged end to exert a desired pressure against the nasal wall. As a force is applied to the locked members the mating teeth disengage to enable hinged movement of the arms. When the nostril cavity is expanded sufficiently the teeth can be interlocked to retain the arms in the new/expanded condition. When the arms (508) and (511) are hingedly displaced in relation to the applied force, the shoulder portion (506) is correspondingly displaced outwardly about the living hinge (507) to enable the enlarged surface area (504) of the shoulder to exert a positive pressure against the internal walls of a nasal cavity.

In this embodiment the device can be adjusted manually insitu to open the nasal cavity. The upstanding support members of the device brace against one side of a nasal cavity while the shoulder portion (506) is pivotable about hinge (507) in concert with hinged movement of arm members (508) and (511) on application of an external force. The bridge (501) prevents the device from being inadvertently inhaled by a user and acts as a rigid support for bracing a surface of the nasal cavity wall. When the device adopts an expanded condition the enlarged end and the upright member(s) brace against the walls of the cavity and effectively prevent inadvertent removal of the device from the cavity.

Figure 27:
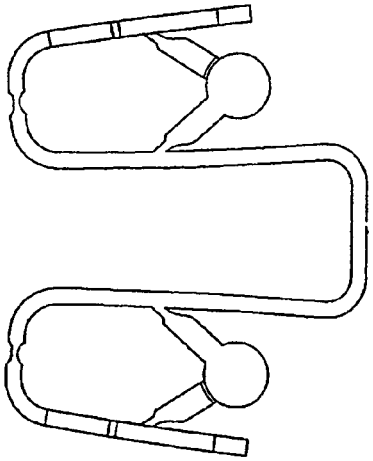
FIG. 27 is a perspective view of a further embodiment in accordance with the present invention.
Figure 27:
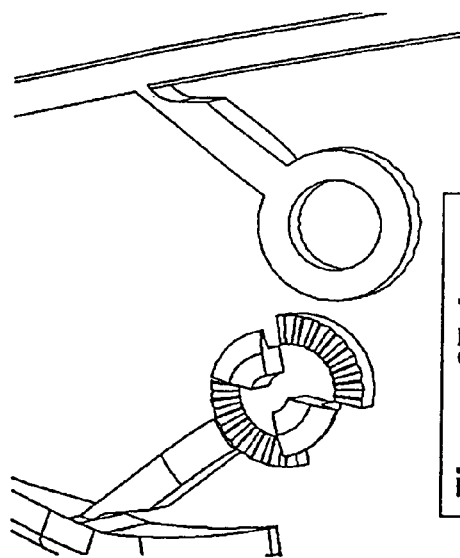
Figure 25:
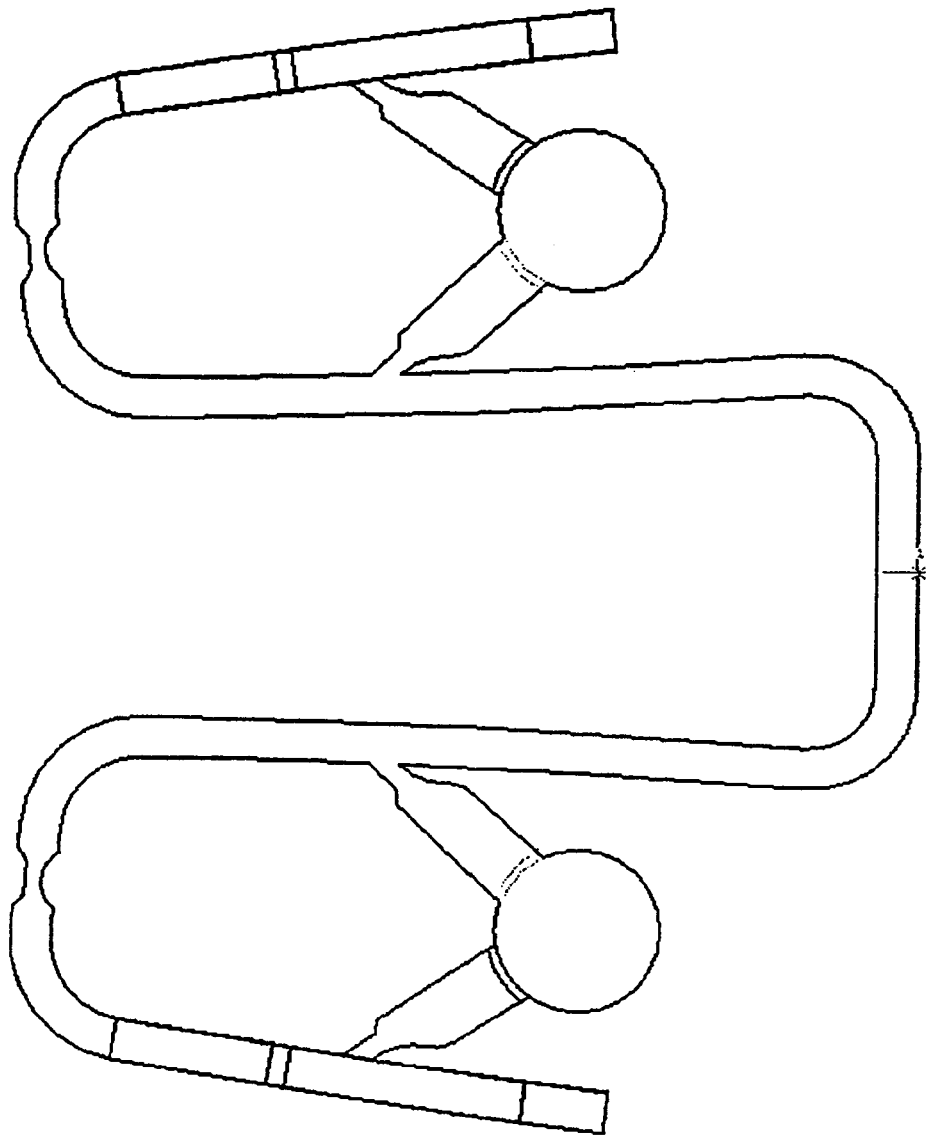
Figure 27:
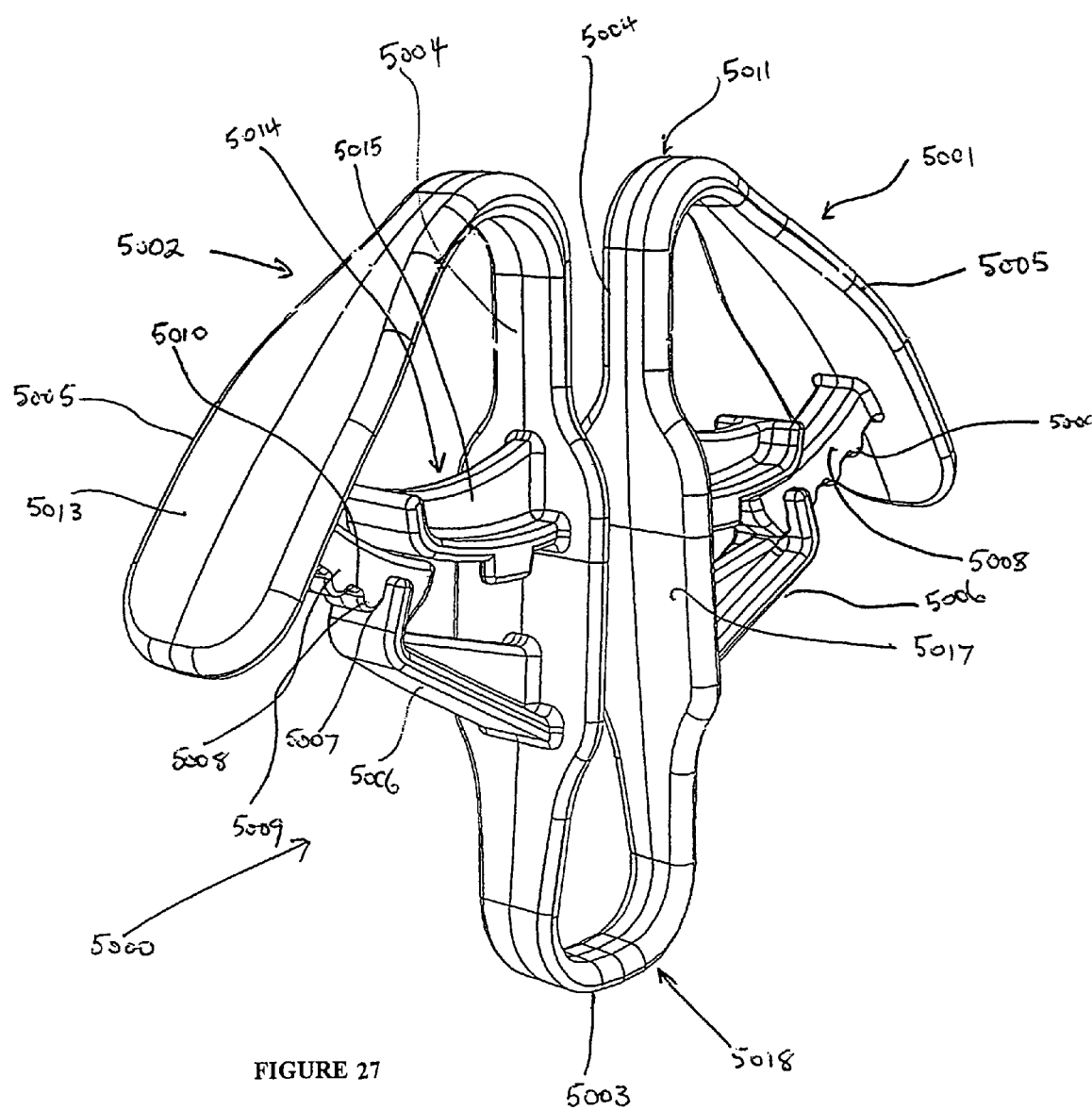

Referring to FIG. 27 there is shown a modification of the device illustrated in FIGS. 22A, B and C. The modified nasal dilation device (5000) is preferably moulded from a plastics material in a single step process and includes a first (5001) and second deformable body (5002) connected by a U-shaped bridge member (5003). Each of the first and second deformable bodies includes a spine (5004) ending in outwardly extending ribs or wings (5005) inclined at an angle to the spine. The bodies each have a set of adjustment members to deflect the ribs relative to the spine consisting of:

> a first arm member (5006) mounted on the spine, which extends outwardly towards the rib (5005) and includes a recess (5007) proximal to the end of the arm. Each of the ribs (5005) includes an inwardly extending arm (5008), each of the arms (5008) include a series of ridges or teeth (5009) separated by adjacent troughs (5010) for interengaging with the recess (5007) on the first arm member (5006). The first arm members (5006) are generally biased so that when a ridge (5009) is passed over the recess (5007) by means of an applied force the first arm member is deflected downwardly towards the bridge until the first arm member resumes its biased position by engagement with an adjacent trough.

Figure 28A:
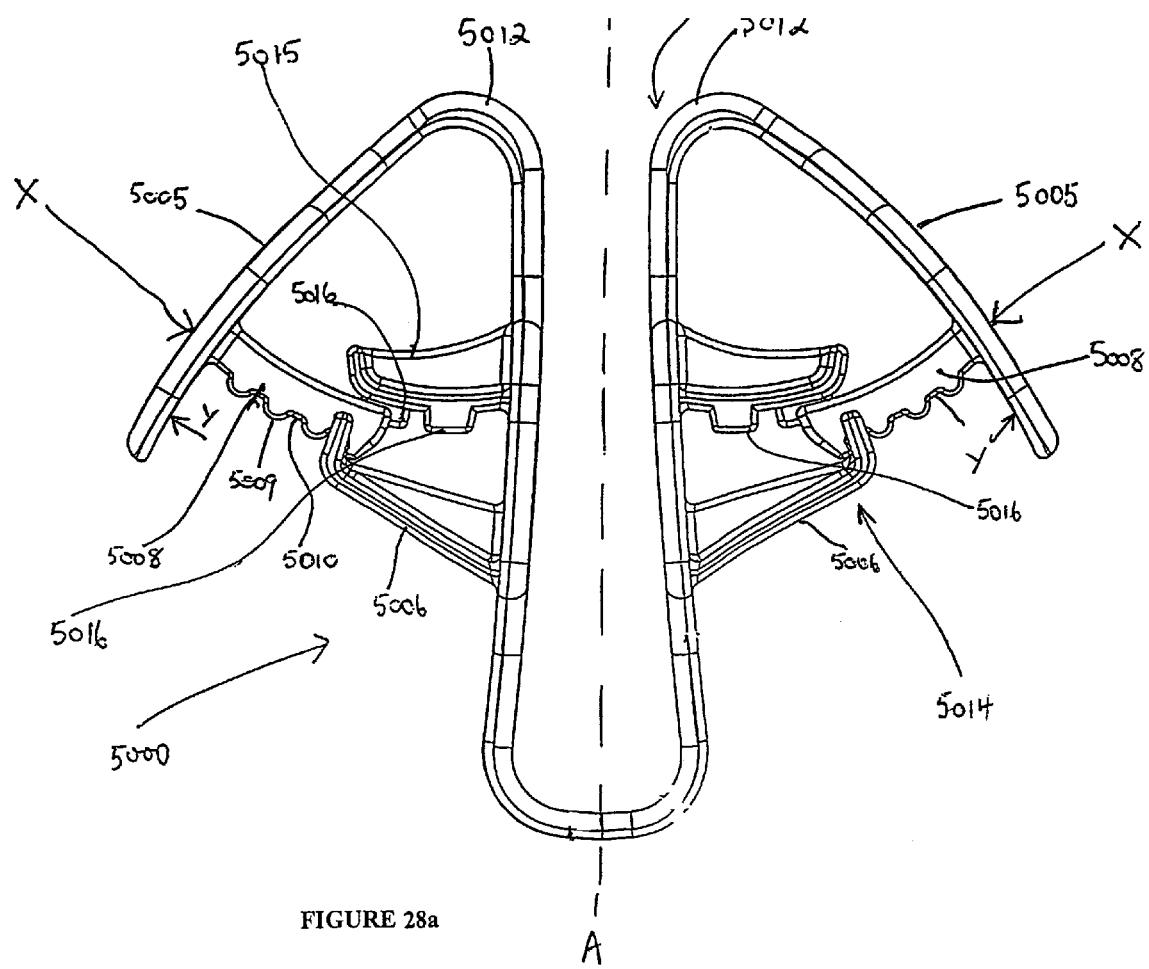
FIGS. 28a, b and c represent the embodiment referred to in FIG. 27 in a front elevation, a plan view from beneath, and a plan view from above respectively.
Figure 28B:
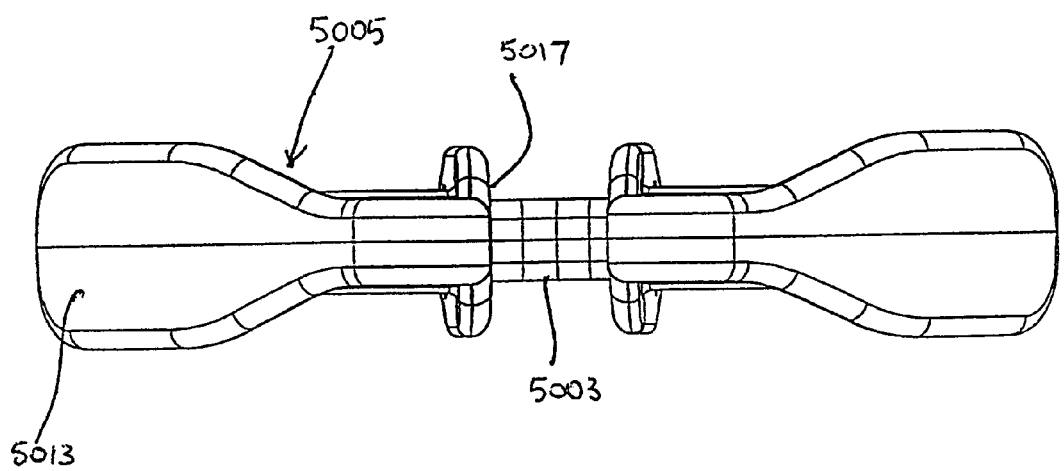
Figure 28C:
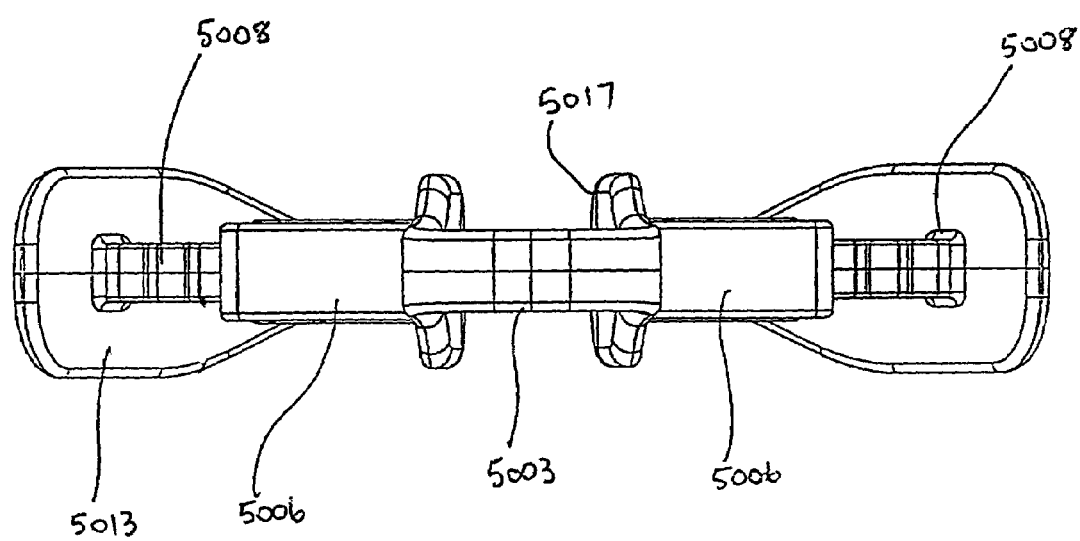

As different troughs are engaged within the recess the angle between the ribs and the spine varies. As is shown in FIG. 28a the first and second deformable bodies exhibit an expanded condition for nasal cavity dilation. Reversing the direction of an applied force can enable the deformable bodies to retract.

The modified device (5000) is symmetrical about axis A—A, best seen in FIG. 28a, hence for convenience an explanation is provided for one half of the device which will in turn apply for the equivalent opposite symmetrical feature.

The uppermost part (5011) of the generally U-shaped spine ends in a rib or wing member (5005) extending outwardly at an angle to the spine (5004) and being connected thereto by a curved section (5012). The rib or wing member (5005) includes a flattened section (5013), which in an operating condition rests against internal wall surfaces of a nasal cavity. The flattening and broadening of the wing section serves to increase the surface area in contact with internal cavity walls to spread the concentration of force exerted by the device over a wider surface as practicable.

In a further embodiment the adjusting means (5014) includes a first arm member (5006) and a second arm member (5015) both mounted to the spine and extending outwardly from the spine and being spaced apart one above the other. The second arm member (5015) includes a pair of oppositely disposed downwardly extending flanges (5016) being spaced apart to both receive and assist alignment of the arm member (5008) therebetween. The first arm member (5006) includes a u-shaped recess (5007) adjacent its end for receiving troughs (5010). When troughs (5010) are engaged within the recess (5007), adjacent ridges or teeth (5009) rest on either side of the recess (5007) to maintain the rib or wing member (5005) in a locked position so that the angle between the ribs and spine (5004) is kept constant to maintain a desired cavity dilation.

The arm members (5006 and 5015) are resiliently mounted on the spine (5004) so that, when an external force is applied to the rib or wing members (5005) in the direction indicated by arrows (x or y), teeth members (5009) cause downward deflection of the first arm (5006) as a tooth acts on a surface of the recess until an adjacent trough (5010) is engaged within the recess (5007). In this way adjustment of the angle between the wing member and the spine can occur to arrive at an expanded or retracted position for dilation of the nasal cavity or to assist removal of the device from the cavity. For example, referring to FIG. 28a, if it is desired to reduce the angle between the wing member and the spine, a user/wearer is able to attend to adjustment by applying an external force against flattened sections (5013) of the wing member in the direction of (X). Similarly applying an external force in the direction of 'Y' can derive an expanded condition for dilating a nasal cavity.

In an insertion condition a trough closest to the wing member is engaged within the recess (5007) so that the angle between the wing and the spine of the body is reduced. This enables easy insertion. Once inserted in a nasal cavity a user can apply an outwardly directed force in situ on a lower inner surface of the wing member in the direction of 'Y'. Once the wing member is expanded sufficiently to promote increased airflow, the angle between the wing and the body is maintained by firm engagement between a trough and the recess adjacent the first arm member.

In use the lowermost portion or bridge (5003) of the device is seated outside the nasal septum and the spine includes flattened portions (5017), which abuts internal wall structure of a nasal cavity. Generally at least the lower most portion (5018) of the device is transparent or flesh coloured so as to render the device inconspicuous from a casual observer.

Figure 29:
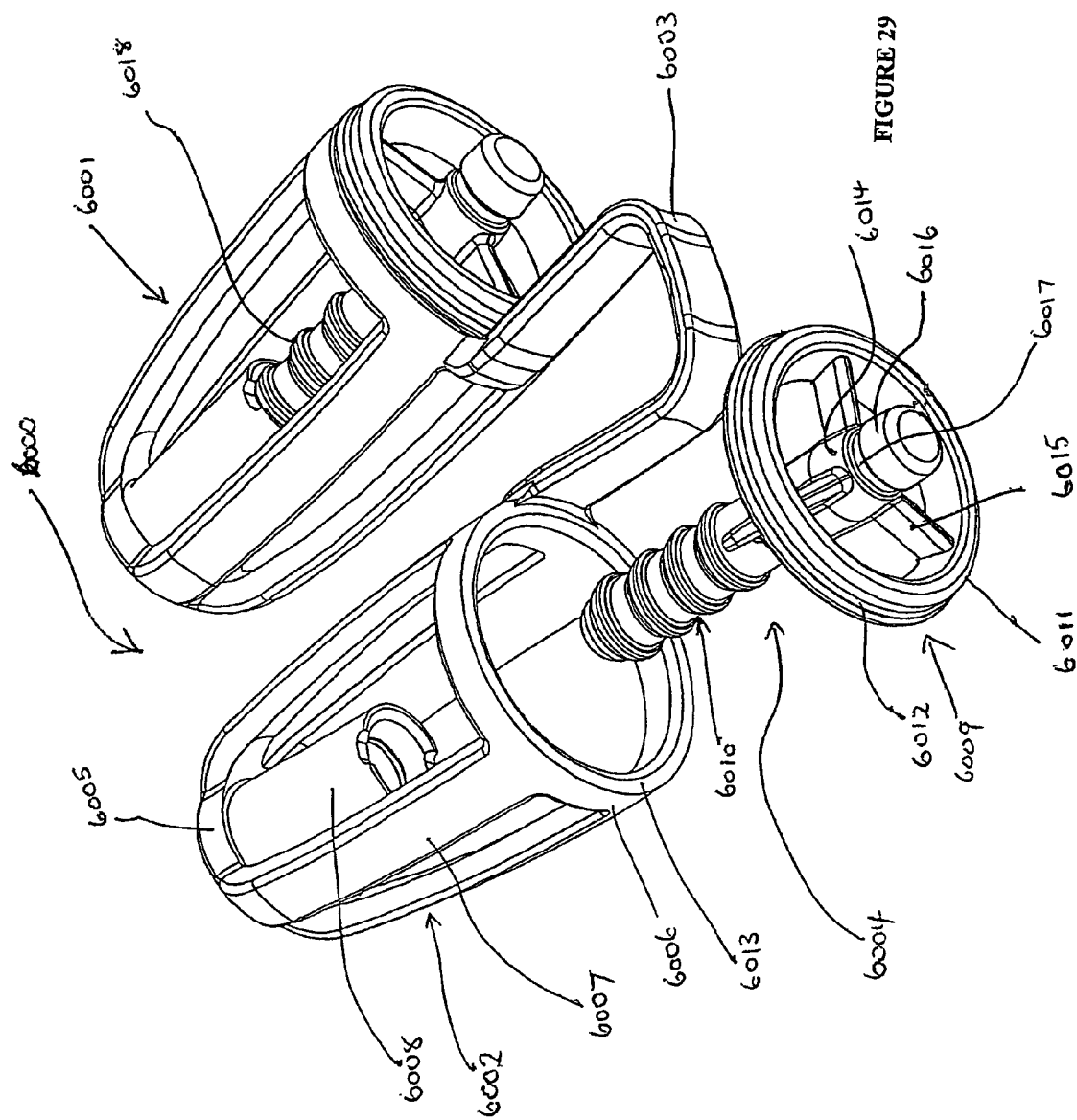
FIG. 29 is a perspective view of an alternative embodiment of the invention in partially assembled condition.
Figure 30A:
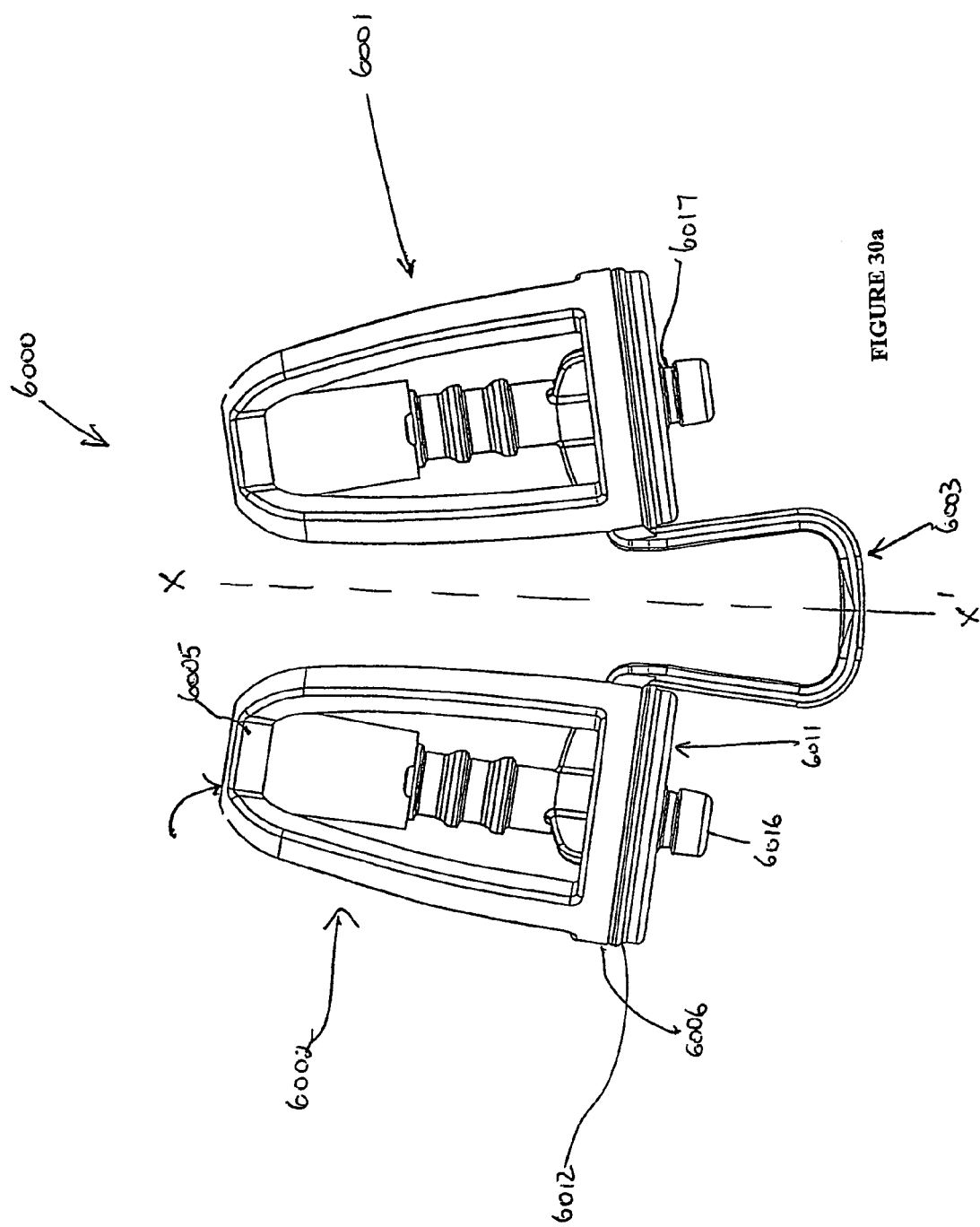
FIGS. 30a, b and c represents the embodiment referred to in FIG. 29 by way of a front elevation, a plan view from above, and a plan view from beneath respectively.

Referring to FIGS. 29 and 30a, b and c there is shown a modification of the cage dilation system embodied in FIG. 20. The cage dilation system (6000) includes a first (6001) and second (6002) deformable bodies connected by a bridge (6003) and an adjustment means (6004). Each of the first and second deformable bodies includes an uppermost substantially circular open end forming a collar (6005) and a lowermost substantially circular open end forming a waistband (6006). A series of spaced apart ribs (6007) connect the uppermost and lowermost ends and the each body has a central hollow cylindrical member (6008) mounted on the collar, which extends within the body towards the lowermost end. For ease of explanation only one body will be described, the remaining body having identical features. The adjustment means (6004) in this embodiment is a closing compression member, which is adapted to engage with the body. The compression member includes a holding base or a foot (6009) and a central leg (6010) mounted thereon, which leg is able to extend into the deformable body with the holding base engaging the waistband of the deformable body.

The compression means comprises a leg or shaft (6010) extending upwardly and centrally located from the foot or holding base (6009). The holding base includes a locking ring (6011), which has an annular shoulder (6012) that abuts the rim (6013) of the waistband when the shaft (6010) is engaged within the hollow cylinder (6008).

The holding base has a central platform (6014) from which the shaft (6010) extends upwardly to be received within the hollow cylinder (6008). The holding base also includes integral radial arm members (6015) connecting the central platform to the locking ring member. The central platform includes a protrusion (6016) extending beneath the level of the locking ring. The protrusion has a recess (6017) (best seen in FIG. 30a) in or about which a vapour delivery system can be housed (not shown).

The shaft (6010) has a series of spaced protrusions (6018) along its length which positively engage the internal surface of the hollow cylinder in an operating condition. It is generally understood that the internal diameter of the hollow cylinder is less than the external diameter of the protrusions so as to enable the protrusions to both deflect and positively engage the hollow cylinder as it moves through the cylinder.

Figure 30B:
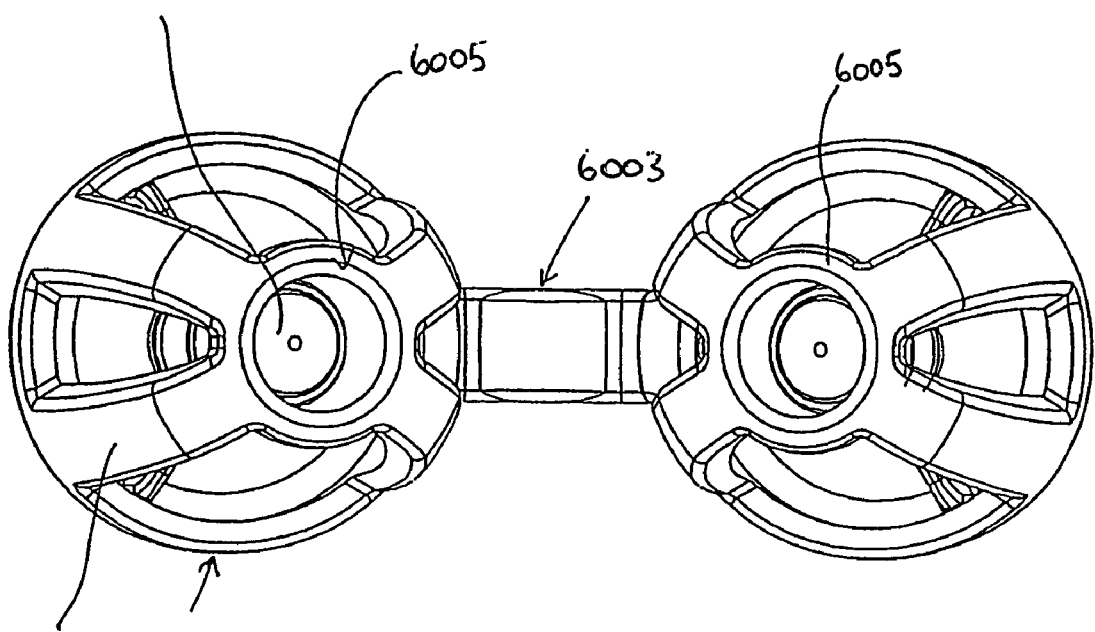
Figure 30C:
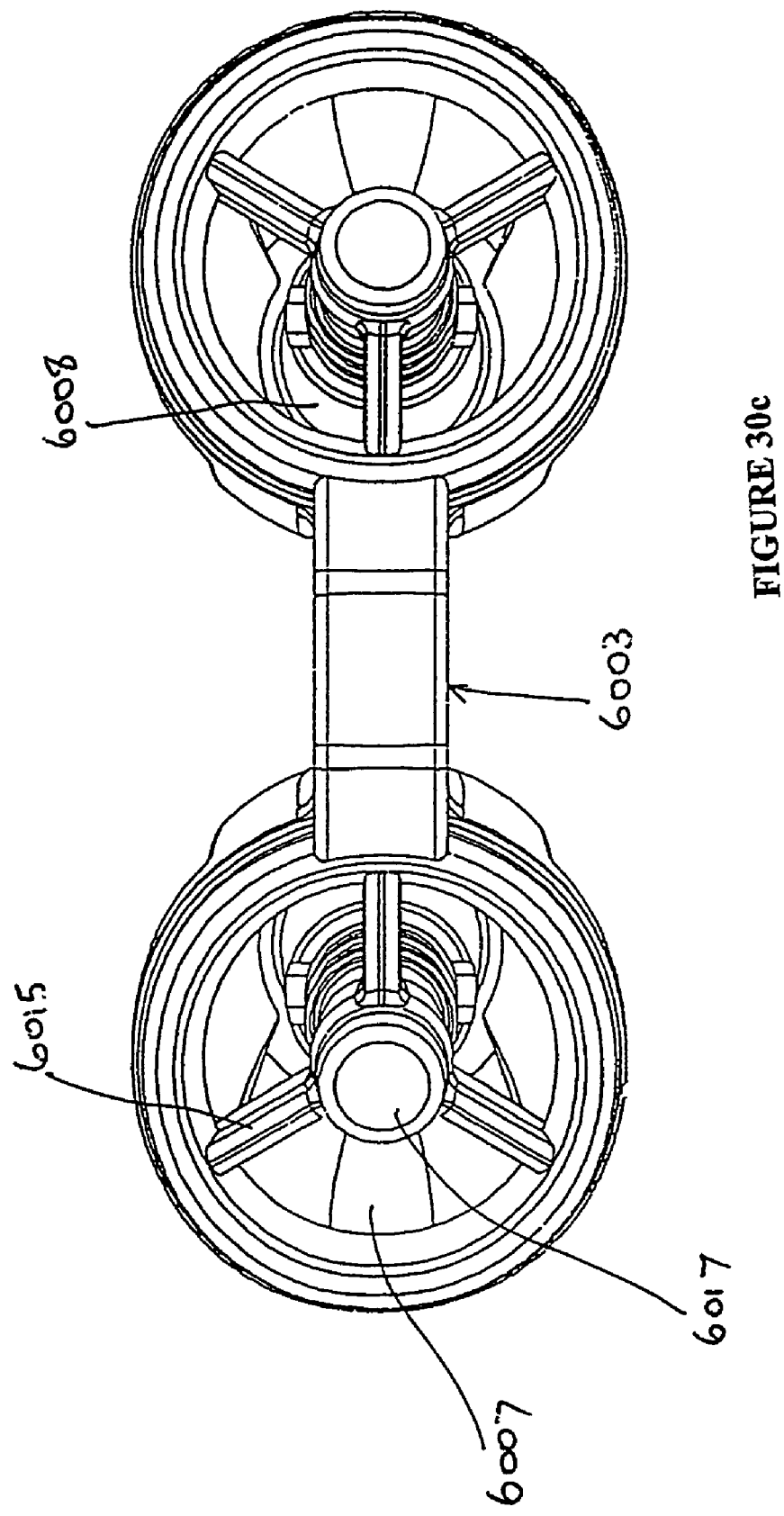

The embodiment illustrated in FIGS. 29 to 30a, b and c shows the two deformable bodies interconnected by a U-shaped bridge (6003). The two deformable bodies exhibit symmetry about vertical axis XX', hence for convenience where reference is made to one body an identical component is present on the second body part. The series of spaced ribs (6007) deflect outwardly from the body describing an arcurate pathway (not shown) when the closing compression member exerts a force against the waistband causing the waistband to be displaced towards the uppermost end.

In an operating condition (seen in FIG. 30a) the shaft (6010) is displaced through the opening of the hollow cylinder by applying an external force between the locking ring on the compression means and the collar. Generally in this embodiment the cage system is fabricated from a resilient plastic material so that when the shaft enters the opening in the hollow cylinder the protrusions (6018) act against the internal surfaces of the hollow cylinder, thereby deflecting the internal surfaces to enable displacement and enabling positive engagement therewith. As the shaft is displaced along the hollow cylinder the ribs deflect outwardly to describe an arcurate pathway. In use the ribs rest against internal wall surfaces of a users nasal cavity. When applying a compressive force between the collar and the waistband causing deflection of the ribs, the walls of the nasal cavity against which the ribs are at rest, extend in response to the outward deflection of the ribs to promote flow of air through the cavity.

The invention claimed is:

1. An adjustable nasal cavity dilation device including:
   a first deformable body, the body having a shape corresponding to the nasal cavity so as to enable insertion of the device within the nasal cavity; the body further including: top and bottom frame ends interconnected by a flexible wall structure, wherein the flexible wall structure undergoes deformation in response to movement of one frame end relative to the other;
   a releasable holding member including complementary mating components that engage with the top and bottom frame ends adapted to maintain the top and bottom frame ends at a desired distance in a holding condition such that deformation of the flexible wall structure is effective for urging against nasal cavity walls to substantially increase air flow through the nasal passage;
   wherein the releasable holding member includes:
      a holding base frame mountable on the bottom frame end of the first deformable body, the base frame having an upstanding member centrally located of the flexible wall structure when the base frame is mounted on the bottom frame, wherein at least a part of the upstanding member includes a series of circumferential teeth;
      a tubular sleeve member extending downwardly from the top frame end of the first deformable body for receiving the upstanding member, at least a part of the sleeve including complimentary internal teeth adapted to engage with the circumferential teeth;
      whereby the upstanding member is received within the sleeve member upon application of an external force to one or both of the frame ends and thereafter the top and bottom frame ends are maintained at a desired distance and allowing sizing of the flexible wall to exert a dilation force on the nasal cavity walls; and
   wherein the holding base frame includes a suspension platform interconnected thereto for housing a medicament such as menthol whereby the suspension platform extends within the body of the device so that the medicament is suspended out of direct surface contact with wall surfaces of the nasal cavity.

2. A nasal dilation device for improving airflow through a nasal cavity including:
   a first deformable body;
   the first deformable body having an uppermost substantially circular open end forming a collar and a lowermost substantially circular open end forming a waistband;
   a series of spaced ribs connecting between the uppermost and lowermost ends, the body including a central member mounted on the collar and extending longitudinally within the body towards the lowermost end;
   a holding base having a central leg mounted thereon, which leg is able to extend into the first deformable body with the holding base engaging the waistband of the first deformable body;
   the leg of the holding base and the central member of the first deformable body having complementary engagement means allowing engagement which causes the holding base to act against the waistband in response to an external force so that the ribs are deflected outwardly of the body to a desired size for dilating the nasal cavity;
   wherein the holding base includes a locking ring interconnected to a platform by a series of radial arms, the locking ring including an annular shoulder that abuts the waistband when the leg engages within the central member.

3. A nasal dilation device for improving airflow through a nasal cavity including:
   a first deformable body;
   the first deformable body having an uppermost substantially circular open end forming a collar and a lowermost substantially circular open end forming a waistband;
   a series of spaced ribs connecting between the uppermost and lowermost ends, the body including a central member mounted on the collar and extending longitudinally within the body towards the lowermost end;
   a holding base having a central leg mounted thereon, which leg is able to extend into the first deformable body with the holding base engaging the waistband of the first deformable body;
   the leg of the holding base and the central member of the first deformable body having complementary engagement means allowing engagement which causes the holding base to act against the waistband in response to an external force so that the ribs are deflected outwardly of the body to a desired size for dilating the nasal cavity;
   wherein the holding base includes a recessed protrusion for receiving a vapor delivery system.

* * * * *